US011192956B2

(12) United States Patent
Matsumura et al.

(10) Patent No.: US 11,192,956 B2
(45) Date of Patent: Dec. 7, 2021

(54) ANTIBODY BINDING TO TMEM132A, ANTICANCER AGENT, AND CANCER TEST METHOD

(71) Applicants: NATIONAL CANCER CENTER JAPAN, Tokyo (JP); RIN INSTITUTE INC., Tokyo (JP)

(72) Inventors: Yasuhiro Matsumura, Kashiwa (JP); Masahiro Yasunaga, Kashiwa (JP); Shinji Saijo, Kashiwa (JP); Shingo Hanaoka, Kashiwa (JP)

(73) Assignees: NATIONAL CANCER CENTER JAPAN, Tokyo (JP); RIN INSTITUTE INC., Tokyo (JP)

( * ) Notice: Subject to any disclaimer, the term of this patent is extended or adjusted under 35 U.S.C. 154(b) by 357 days.

(21) Appl. No.: 16/325,315

(22) PCT Filed: Aug. 14, 2017

(86) PCT No.: PCT/JP2017/029251
§ 371 (c)(1),
(2) Date: Mar. 15, 2019

(87) PCT Pub. No.: WO2018/034259
PCT Pub. Date: Feb. 22, 2018

(65) Prior Publication Data
US 2019/0225704 A1     Jul. 25, 2019

(30) Foreign Application Priority Data
Aug. 15, 2016   (JP) .............................. JP2016-159342

(51) Int. Cl.
*C07K 16/30* (2006.01)
*A61P 43/00* (2006.01)
*A61K 45/00* (2006.01)
*G01N 33/53* (2006.01)
*G01N 33/574* (2006.01)
*A61P 35/00* (2006.01)
*A61K 39/395* (2006.01)
*C07K 16/28* (2006.01)
*A61K 47/68* (2017.01)
*C12N 15/09* (2006.01)

(52) U.S. Cl.
CPC ............ *C07K 16/30* (2013.01); *A61K 39/395* (2013.01); *A61K 45/00* (2013.01); *A61K 47/6803* (2017.08); *A61K 47/6851* (2017.08); *A61P 35/00* (2018.01); *A61P 43/00* (2018.01); *C07K 16/28* (2013.01); *G01N 33/53* (2013.01); *G01N 33/574* (2013.01); *G01N 33/57419* (2013.01); *C07K 2317/565* (2013.01); *C12N 15/09* (2013.01)

(58) Field of Classification Search
CPC .. C07K 16/30; C07K 16/28; C07K 2317/565; A61P 43/00; A61P 35/00; A61K 45/00; A61K 39/395; A61K 47/6851; A61K 47/6803; G01N 33/53; G01N 33/574; G01N 33/57419; C12N 15/09
See application file for complete search history.

(56) References Cited

U.S. PATENT DOCUMENTS

| 2011/0137016 A1 | 6/2011 | Dennis et al. |
| 2011/0319282 A1 | 12/2011 | Garcia Bilbao et al. |
| 2017/0260284 A1 | 9/2017 | Matsumura et al. |

FOREIGN PATENT DOCUMENTS

| EP | 2169078 A1 * | 3/2010 | ........... C12Q 1/6886 |
| EP | 2669682 A1 | 12/2013 | |
| JP | 2010-268690 A | 12/2010 | |
| JP | 2016-104752 A | 6/2016 | |
| WO | WO-2016/039321 A1 | 3/2016 | |

OTHER PUBLICATIONS

Kim, et al. Biomol Ther (Seoul) 2015; 23(6): 493-509 (Year: 2015).*
Sela—Culang Front. Immunol. 4(302) (2013) (Year: 2013).*
Almagro & Fransson, Frontiers in Bioscience 2008; 13:1619-33 (Year: 2008).*
Marchalonis et al., Dev & Comp Immunol 30:223-247 (2006) (Year: 2006).*
Edwards et al., J Mol Biol 334:103-118 (2003) (Year: 2003).*
Extended European Search Report for European Application No. 17841481.9, dated Mar. 5, 2020 (8 pages).
Garcia-Bilbao et al., "Identification of a biomarker panel for colorectal cancer diagnosis," BMC Cancer 12:43 (2012) (13 pages).
Oh-hashi et al., "Characterization of the expression and cell-surface localization of transmembrane protein 132A," Mol. Cell. Biochem. 370(1-2): 23-33 (2012).
Oh-hashi et al., "Transcriptional and post-transcriptional regulation of transmembrane protein 132A," Mol. Cell Biochem. 405(1-2): 291-299 (2015).
Cunningham et al., "Cetuximab monotherapy and cetuximab plus irinotecan in irinotecan-refractory metastatic colorectal cancer," N. Engl. J. Med. 351(4):337-345 (2004).
Goldstein et al., "Biological efficacy of a chimeric antibody to the epidermal growth factor receptor in a human tumor xenograft model," Clin. Cancer Res. 1(11):1311-1318 (1995).
International Search Report dated Sep. 26, 2017 for International Patent Application No. PCT/JP2017/029251, Matsumura et al., "Antibody Binding to TMEM132A, Anticancer Agent, and Cancer Test Method," filed Aug. 14, 2017 (6 pages).
Karapetis et al., "K-ras mutations and benefit from cetuximab in advanced colorectal cancer," N. Engl. J. Med. 359(17):1757-1765 (2008).

(Continued)

Primary Examiner — Julie Wu
Assistant Examiner — John L Van Druff
(74) Attorney, Agent, or Firm — Clark & Elbing LLP; Susan M. Michaud

(57) ABSTRACT

[Problem]
The present invention provides an antibody that binds to TMEM132A, an anticancer agent and a cancer test method.
[Solution]
An antibody that binds to TMEM132A.

12 Claims, 6 Drawing Sheets
Specification includes a Sequence Listing.

(56) References Cited

OTHER PUBLICATIONS

Oh-hashi et al., "GRP78-binding protein regulates cAMP-induced gilal fibrillary acidic protein expression in rat C6 glioblastoma cells," FEBS Lett. 580(16):3943-3947 (2006).

Oh-hashi et al., "Knockdown of transmembrane protein 132A by RNA interference facilitates serum starvation-induced cell death in Neuro2a cells," Mol. Cell Biochem. 342(1-2):117-123 (2010).

Shimosato et al., "Distinctive expression of TMEM132A and its regulation after the nerve injury in the DRG," Biomed. Res. Clin. Prac. 1(3):109-111 (2016) (3 pages).

* cited by examiner

Brain

Cardiac tissue

Lung

Liver

Kidney

Small intestine

Skin

ANTIBODY BINDING TO TMEM132A, ANTICANCER AGENT, AND CANCER TEST METHOD

TECHNICAL FIELD

The present invention provides an antibody that binds to TMEM132A, an anticancer agent and a cancer test method.

BACKGROUND ART

Recently, a large number of molecular target drugs, which specifically act on predetermined molecules, have been developed as an anticancer agent. Particularly, various antibody drugs have been developed which recognizes, as antigens, molecules expressed specifically on certain cancer cells and molecules expression of which on cancer cells are elevated. In development of the antibody drugs, first, a molecule specifically expressed in a cancer tissue alone or a molecule whose expression is elevated in a cancer tissue, is specified by comparing expression of mRNAs in the cancer tissue collected in a surgical operation to the expression of mRNAs in a normal tissue taken from the tissue in the vicinity of the cancer tissue, and then, an antibody is prepared using the molecule as an antigen.

Colorectal cancer is a cancer developed from colonic mucosal cells. Up to present, cetuximab, which is an antibody targeting an epidermal growth factor receptor (EGFR), has been developed and used for colorectal cancer (Non Patent Literatures 1-3). However, since EGFR is also expressed in normal tissues, cetuximab has a possibility of acting on the normal tissues. Because of this, development of a molecular target drug, targeting more specifically to a molecule expressed in colorectal cancer, has been desired. With this point, there has been a problem: since the mucosal tissue where colorectal cancer develops is present only slightly, it is difficult to specify a target molecule by comparing the cancerous mucosal cells to normal mucosal cells. In connection with this, TMEM-180 has been developed as a candidate target molecule (Patent Literature 1).

CITATION LIST

Patent Literature

Patent Literature 1: WO2016039321A1

Non Patent Literature

Non Patent Literature 1: Cunningham D. et al., The New England Journal of Medicine., Vol. 351, No. 4, 2004, p.p. 337-345.
Non Patent Literature 2: Goldstein N I. Et al., Clin Cancer Res. Vol. 1, 1311-1318, 1995.
Non Patent Literature 3: Karapetis C S. Et al., The New Engl J Med. Vol. 359, 1757-1765.

SUMMARY OF INVENTION

The present invention provides an antibody that binds to TMEM132A, an anticancer agent and a cancer test method.

The present inventors found that TMEM132A protein is expressed specifically in cancer. They also found that the expression or non-expression of TMEM132A protein can be used especially in diagnosis of colorectal cancer. They further found that TMEM132A protein is expressed on the surface on cancer cells, and that an antibody that binds to TMEM132A protein can bind to the surface of the cancer cells. The present invention was made based on these findings.

According to the present invention, for example, the following inventions are provided.

[1] An antibody that binds to TMEM132A, or an antigen-binding fragment thereof, wherein the antibody is selected from the group consisting of:

(1) an antibody comprising a heavy chain variable region comprising a heavy chain CDR1 having an amino acid sequence set forth in SEQ ID NO: 1, a heavy chain CDR2 having an amino acid sequence set forth in SEQ ID NO: 2 and a heavy chain CDR3 having an amino acid sequence set forth in SEQ ID NO: 3, and a light chain variable region comprising a light chain CDR1 having an amino acid sequence set forth in SEQ ID NO: 5, a light chain CDR2 having an amino acid sequence set forth in SEQ ID NO: 6 and a light chain CDR3 having an amino acid sequence set forth in SEQ ID NO: 7;

(2) an antibody comprising a heavy chain variable region comprising a heavy chain CDR1 having an amino acid sequence set forth in SEQ ID NO: 9, a heavy chain CDR2 having an amino acid sequence set forth in SEQ ID NO: 10 and a heavy chain CDR3 having an amino acid sequence set forth in SEQ ID NO: 11, and a light chain variable region comprising a light chain CDR1 having an amino acid sequence set forth in SEQ ID NO: 13, a light chain CDR2 having an amino acid sequence set forth in SEQ ID NO: 14, and a light chain CDR3 having an amino acid sequence set forth in SEQ ID NO: 15;

(3) an antibody comprising a heavy chain variable region comprising a heavy chain CDR1 having an amino acid sequence set forth in SEQ ID NO: 17, a heavy chain CDR2 having an amino acid sequence set forth in SEQ ID NO: 18 and a heavy chain CDR3 having an amino acid sequence set forth in SEQ ID NO: 19, and a light chain variable region comprising a light chain CDR1 having an amino acid sequence set forth in SEQ ID NO: 5, a light chain CDR22 having an amino acid sequence set forth in SEQ ID NO: 21 and a light chain CDR23 having an amino acid sequence set forth in SEQ ID NO: 7;

(4) an antibody comprising
a heavy chain variable region comprising a heavy chain CDR1 having an amino acid sequence set forth in SEQ ID NO: 25, a heavy chain CDR2 having an amino acid sequence set forth in SEQ ID NO: 26 and a heavy chain CDR3 having an amino acid sequence set forth in SEQ ID NO: 27, and a light chain variable region comprising a light chain CDR1 having an amino acid sequence set forth in SEQ ID NO: 29, a light chain CDR2 having an amino acid sequence set forth in SEQ ID NO: 30, and a light chain CDR3 having an amino acid sequence set forth in SEQ ID NO: 31;

(5) an antibody that competes with any one of the antibodies (1) to (4) for binding to TMEM132A; and (6) an antibody having an insertion, substitution, deletion or addition of one to several amino acids in any one of the amino acid sequences of the antibodies (1) to (4) and the CDRs thereof.

[2] The antibody or an antigen-binding fragment according to the above [1], wherein the antibody is (1) an antibody comprising a heavy chain variable region comprising a heavy chain CDR1 having an amino acid sequence set forth in SEQ ID NO: 1, a heavy chain CDR2 having an amino acid sequence set forth in SEQ ID NO: 2 and a heavy chain CDR3 having an amino acid sequence set forth in SEQ ID NO: 3, and a light chain variable region comprising a light chain CDR1 having an amino acid sequence set forth in SEQ ID NO: 5, a light chain CDR2 having an amino acid sequence set forth in SEQ ID NO: 6 and a light chain CDR3 having an amino acid sequence set forth in SEQ ID NO: 7, or an antibody that competes with the antibody described in the above (1) for binding to TMEM132A.

[3] The antibody or an antigen-binding fragment thereof according to the above [2], comprising a heavy chain variable region having an amino acid sequence of a heavy chain variable region set forth in SEQ ID NO: 4 and a light chain variable region having an amino acid sequence of a light chain variable region set forth in SEQ ID NO: 8.

[4] The antibody or an antigen-binding fragment thereof according to the above [1], wherein the antibody is (2) an antibody comprising a heavy chain variable region comprising a heavy chain CDR1 having an amino acid sequence set forth in SEQ ID NO: 9, a heavy chain CDR2 having an amino acid sequence set forth in SEQ ID NO: 10 and a heavy chain CDR3 having an amino acid sequence set forth in SEQ ID NO: 11, and a light chain variable region comprising a light chain CDR1 having an amino acid sequence set forth in SEQ ID NO: 13, a light chain CDR2 having an amino acid sequence set forth in SEQ ID NO: 14, and a light chain CDR3 having an amino acid sequence set forth in SEQ ID NO: 15, or an antibody that competes with the antibody according to the above (2) for binding to TMEM132A.

[5] The antibody or an antigen-binding fragment thereof according to the above [4], comprising a heavy chain variable region having an amino acid sequence of a heavy chain variable region set forth in SEQ ID NO: 12, and a light chain variable region having an amino acid sequence of a light chain variable region set forth in SEQ ID NO: 16.

[6] The antibody or an antigen-binding fragment thereof according to the above [1], wherein the antibody is (3) an antibody comprising a heavy chain variable region comprising a heavy chain CDR1 having an amino acid sequence set forth in SEQ ID NO: 17, a heavy chain CDR2 having an amino acid sequence set forth in SEQ ID NO: 18 and a heavy chain CDR3 having an amino acid sequence set forth in SEQ ID NO: 19, and a light chain variable region comprising a light chain CDR1 having an amino acid sequence set forth in SEQ ID NO: 5, a light chain CDR22 having an amino acid sequence set forth in SEQ ID NO: 21 and a light chain CDR23 having an amino acid sequence set forth in SEQ ID NO: 7; or an antibody that competes with the antibody described in the above (3) for binding to TMEM132A.

[7] The antibody or an antigen-binding fragment thereof according to the above [6], comprising a heavy chain variable region having an amino acid sequence of a heavy chain variable region set forth in SEQ ID NO: 20, and a light chain variable region having an amino acid sequence of a light chain variable region set forth in SEQ ID NO: 24.

[8] The antibody or an antigen-binding fragment thereof according to the above [1], wherein the antibody is (4) an antibody comprising a heavy chain variable region comprising a heavy chain CDR1 having an amino acid sequence set forth in SEQ ID NO: 25, a heavy chain CDR2 having an amino acid sequence set forth in SEQ ID NO: 26 and a heavy chain CDR3 having an amino acid sequence set forth in SEQ ID NO: 27, and a light chain variable region comprising a light chain CDR1 having an amino acid sequence set forth in SEQ ID NO: 29, a light chain CDR2 having an amino acid sequence set forth in SEQ ID NO: 30, and a light chain CDR3 having an amino acid sequence set forth in SEQ ID NO: 31, or an antibody that competes with the antibody described in the above (4) for binding to TMEM132A.

[9] The antibody or an antigen-binding fragment thereof according to the above [8], comprising a heavy chain variable region having an amino acid sequence of a heavy chain variable region set forth in SEQ ID NO: 28, and a light chain variable region having an amino acid sequence of a light chain variable region set forth in SEQ ID NO: 32.

[10] A diagnostic agent for cancer comprising an antibody that binds to TMEM132A.

[11] The diagnostic agent for cancer according to the above [10], wherein the antibody is the antibody defined in any one of the above [1] to [9].

[12] A method for detecting a cancer cell in a subject, comprising determining whether TMEM132A protein is present or not in a biological sample taken from the subject.

[13] The method for detecting a cancer cell according to the above [12], wherein whether TMEM132A protein is present or not is determined by an antibody that binds to TMEM132A.

[14] The method for detecting a cancer cell according to the above [13], wherein the antibody is the antibody defined in any one of the above [1] to [9].

[15] A pharmaceutical composition for use in treating a cancer, comprising an antibody that binds to TMEM132A.

[16] The pharmaceutical composition according to the above [15], wherein the antibody is the antibody defined in any one of the above [1] to [9].

[17] The pharmaceutical composition according to the above [15] or [16], wherein the antibody is in the form of a conjugate with a cytotoxic agent.

DETAILED DESCRIPTION OF THE INVENTION

Figure 1:
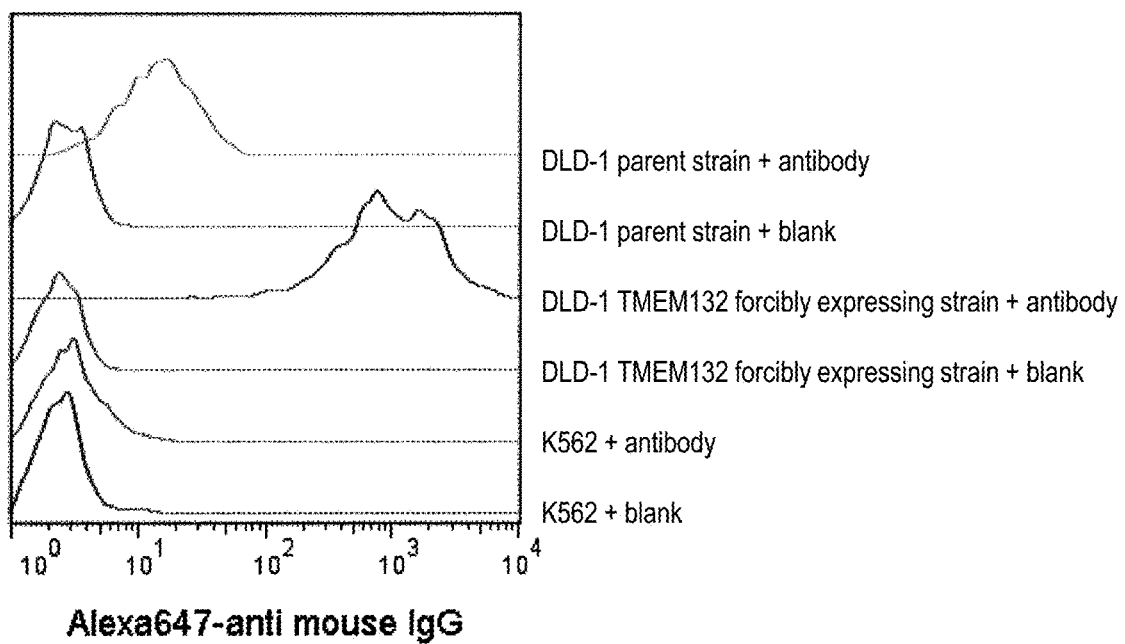
FIG. 1 shows that TMEM132A protein is expressed on the surface of cancer cells.

In the specification, the "subject" can be a mammal and preferably a human. The subject is a subject affected with mesothelioma, another tumor or cancer or having a risk thereof.

In the specification, the "treatment" means therapeutic and prophylactic treatment. Accordingly, in the specification, the "pharmaceutical composition for use in treating a cancer" means a pharmaceutical composition for use in therapeutically or prophylactically treating a cancer and includes an anticancer agent as an example.

In the specification, the "antibody" means an immunoglobulin and includes a polyclonal antibody and a monoclonal antibody. A preferable antibody is a monoclonal antibody. The origin from which an antibody is derived, which is not particularly limited; includes a non-human animal derived antibody, a non-human mammal derived antibody and a human antibody, as examples. The antibody may be a chimeric antibody, a humanized antibody or a human antibody. The antibody may be a bispecific antibody.

The antibody has a structure in which two heavy chains and two light chains are associated. The heavy chain consists of a heavy chain variable region (VH), a heavy chain constant region (CH1), a hinge region and CH2 and CH3; and the light chain consists of a light chain variable region (VL) and a light chain constant region (CL).

In the specification, the "antigen-binding fragment" means a part of an antibody keeping a binding ability to an antigen. The antigen-binding fragment may contain either one or both of a heavy chain variable region and a light chain variable region of the antibody of the present invention. The antigen-binding fragment may be a chimera or humanized. Examples of the antigen-binding fragment include Fab, Fab', F(ab')2, Fv, scFv (single chain Fv), a diabody and sc(Fv)$_2$ (single chain (Fv)$_2$). A fragment of such an antibody, which is not particularly limited, can be obtained, for example, by treating an antibody with an enzyme. For example, if an antibody is digested with papain, Fab can be obtained. Alternatively, if an antibody is digested with pepsin, F(ab')$_2$ can be obtained. If F(ab')$_2$ is further reduced, Fab' can be obtained. In the present invention, a fragment of such an antibody, capable of binding to an antigen can be used.

According to the present invention, there is provided an antibody that binds to TMEM132A, or an antigen-binding fragment thereof, wherein the antibody is selected from the group consisting of:

(1) an antibody comprising a heavy chain variable region comprising a heavy chain CDR1 having an amino acid sequence set forth in SEQ ID NO: 1, a heavy chain CDR2 having an amino acid sequence set forth in SEQ ID NO: 2 and a heavy chain CDR3 having an amino acid sequence set forth in SEQ ID NO: 3, and a light chain variable region comprising a light chain CDR1 having an amino acid sequence set forth in SEQ ID NO: 5, a light chain CDR2 having an amino acid sequence set forth in SEQ ID NO: 6 and a light chain CDR3 having an amino acid sequence set forth in SEQ ID NO: 7;

(2) an antibody comprising a heavy chain variable region comprising a heavy chain CDR1 having an amino acid sequence set forth in SEQ ID NO: 9, a heavy chain CDR2 having an amino acid sequence set forth in SEQ ID NO: 10 and a heavy chain CDR3 having an amino acid sequence set forth in SEQ ID NO: 11, and a light chain variable region comprising a light chain CDR1 having an amino acid sequence set forth in SEQ ID NO: 13, a light chain CDR2 having an amino acid sequence set forth in SEQ ID NO: 14, and a light chain CDR3 having an amino acid sequence set forth in SEQ ID NO: 15;

(3) an antibody comprising a heavy chain variable region comprising a heavy chain CDR1 having an amino acid sequence set forth in SEQ ID NO: 17, a heavy chain CDR2 having an amino acid sequence set forth in SEQ ID NO: 18 and a heavy chain CDR3 having an amino acid sequence set forth in SEQ ID NO: 19, and a light chain variable region comprising a light chain CDR1 having an amino acid sequence set forth in SEQ ID NO: 5, a light chain CDR22 having an amino acid sequence set forth in SEQ ID NO: 21 and a light chain CDR23 having an amino acid sequence set forth in SEQ ID NO: 7; and (4) an antibody comprising a heavy chain variable region comprising a heavy chain CDR1 having an amino acid sequence set forth in SEQ ID NO: 25, a heavy chain CDR2 having an amino acid sequence set forth in SEQ ID NO: 26 and a heavy chain CDR3 having an amino acid sequence set forth in SEQ ID NO: 27, and a light chain variable region comprising a light chain CDR1 having an amino acid sequence set forth in SEQ ID NO: 29, a light chain CDR2 having an amino acid sequence set forth in SEQ ID NO: 30, and a light chain CDR3 having an amino acid sequence set forth in SEQ ID NO: 31;

(5) an antibody that competes with any one of the antibodies (1) to (4) for binding to TMEM132A;

(6) an antibody having an insertion, substitution, deletion or addition of one to several amino acids in any one of the amino acid sequences of the antibodies (1) to (4) and the CDRs thereof;

(7) an antibody having a heavy chain variable region and a light chain variable region having an amino acid sequence identity of 80% or more respectively with the heavy chain variable region and light chain variable region of any one of the antibodies of the above (1) to (4); and (8) an antibody having 1, 2, 3, 4, 5 or all of the CDRs of the antibodies of the above (1) to (4), as CDR(s).

According to the present invention, there is provided an antibody that binds to TMEM132A, or an antigen-binding fragment thereof; more specifically (1) an antibody comprising a heavy chain variable region comprising a heavy chain CDR1 having an amino acid sequence set forth in SEQ ID NO: 1, a heavy chain CDR2 having an amino acid sequence set forth in SEQ ID NO: 2 and a heavy chain CDR3 having an amino acid sequence set forth in SEQ ID NO: 3, and a light chain variable region comprising a light chain CDR1 having an amino acid sequence set forth in SEQ ID NO: 5, a light chain CDR2 having an amino acid sequence set forth in SEQ ID NO: 6 and a light chain CDR3 having an amino acid sequence set forth in SEQ ID NO: 7, an antibody that competes with the antibody described in the above (1) for binding to TMEM132A, an antibody having an insertion, substitution, deletion or addition of one to several amino acids in the amino acid sequence of the antibody described in the above (1) and its CDRs, or an antibody having 1, 2, 3, 4, 5 or all of the CDRs of the antibody described in the above (1), as CDR(s); or an antigen-binding fragment thereof.

According to the present invention, there is provided an antibody that binds to TMEM132A or an antigen-binding fragment thereof, more specifically, (1a) an antibody comprising a heavy chain variable region having an amino acid sequence of a heavy chain variable region set forth in SEQ ID NO: 4, and a light chain variable region having an amino acid sequence of a light chain variable region set forth in SEQ ID NO: 8, an antibody that competes with the antibody described in the above (1a) for binding to TMEM132A, an antibody having an insertion, substitution, deletion or addition of one to several amino acids in any one of the amino acid sequences of the antibody described in the above (1a) and its CDRs, or an antibody having 1, 2, 3, 4, 5 or all of the CDRs of the antibody described in the above (1a), as CDR(s); or an antigen-binding fragment thereof.

According to the present invention, there is provided an antibody that binds to TMEM132A or an antigen-binding fragment thereof, more specifically, (2) an antibody comprising a heavy chain variable region comprising a heavy chain CDR1 having an amino acid sequence set forth in SEQ ID NO: 9, a heavy chain CDR2 having an amino acid sequence set forth in SEQ ID NO: 10 and a heavy chain CDR3 having an amino acid sequence set forth in SEQ ID NO: 11, and a light chain variable region comprising a light chain CDR1 having an amino acid sequence set forth in SEQ ID NO: 13, a light chain CDR2 having an amino acid sequence set forth in SEQ ID NO: 14, and a light chain CDR3 having an amino acid sequence set forth in SEQ ID NO: 15, an antibody that competes with the antibody described in the above (2) for binding to TMEM132A, an antibody having an insertion, substitution, deletion or addition of one to several amino acids in any one of the amino acid sequences of the antibody described in the above (2) and its CDRs, or an antibody having 1, 2, 3, 4, 5 or all of the CDRs of the antibody described in the above (2), as CDR(s); or an antigen-binding fragment thereof.

According to the present invention, there is provided an antibody that binds to TMEM132A or an antigen-binding fragment thereof, more specifically, (2a) an antibody comprising a heavy chain variable region having an amino acid sequence of a heavy chain variable region set forth in SEQ ID NO: 12, and a light chain variable region having an amino acid sequence of a light chain variable region set forth in SEQ ID NO: 16, an antibody that competes with the antibody described in the above (2a) for binding to TMEM132A, an antibody having an insertion, substitution, deletion or addition of one to several amino acids in any one of the amino acid sequences of the antibody described in the above (2a) and its CDRs, or an antibody having 1, 2, 3, 4, 5 or all of the CDRs of the antibody described in the above (2a), as CDR(s); or an antigen-binding fragment thereof.

According to the present invention, there is provided an antibody that binds to TMEM132A or an antigen-binding fragment thereof, more specifically, (3) an antibody comprising a heavy chain variable region comprising a heavy chain CDR1 having an amino acid sequence set forth in SEQ ID NO: 17, a heavy chain CDR2 having an amino acid sequence set forth in SEQ ID NO: 18 and a heavy chain CDR3 having an amino acid sequence set forth in SEQ ID NO: 19, and a light chain variable region comprising a light chain CDR1 having an amino acid sequence set forth in SEQ ID NO: 5, a light chain CDR22 having an amino acid sequence set forth in SEQ ID NO: 21 and a light chain CDR23 having an amino acid sequence set forth in SEQ ID NO: 7, an antibody that competes with the antibody described in the above (3) for binding to TMEM132A, an antibody having an insertion, substitution, deletion or addition of one to several amino acids in any one of the amino acid sequences of the antibody described in the above (3) and its CDRs, or an antibody having 1, 2, 3, 4, 5 or all of the CDRs of the antibody described in the above (3), as CDR(s); or an antigen-binding fragment thereof.

According to the present invention, there is provided an antibody that binds to TMEM132A or an antigen-binding fragment thereof, more specifically, (3a) an antibody comprising a heavy chain variable region having an amino acid sequence of a heavy chain variable region set forth in SEQ ID NO: 20, and a light chain variable region having an amino acid sequence of a light chain variable region set forth in SEQ ID NO: 24, an antibody that competes with the antibody described in the above (3a) for binding to TMEM132A, an antibody having an insertion, substitution, deletion or addition of one to several amino acids in any one of the amino acid sequences of the antibody described in the above (3a) and its CDRs, or an antibody having 1, 2, 3, 4, 5 or all of the CDRs of the antibody described in the above (3a), as CDR(s); or an antigen-binding fragment thereof.

According to the present invention, there is provided an antibody that binds to TMEM132A or an antigen-binding fragment thereof, more specifically, (4) an antibody comprising a heavy chain variable region comprising a heavy chain CDR1 having an amino acid sequence set forth in SEQ ID NO: 25, a heavy chain CDR2 having an amino acid sequence set forth in SEQ ID NO: 26 and a heavy chain CDR3 having an amino acid sequence set forth in SEQ ID NO: 27, and a light chain variable region comprising a light chain CDR1 having an amino acid sequence set forth in SEQ ID NO: 29, a light chain CDR2 having an amino acid sequence set forth in SEQ ID NO: 30, and a light chain CDR3 having an amino acid sequence set forth in SEQ ID NO: 31, an antibody that competes with the antibody described in the above (4) for binding to TMEM132A, an antibody having an insertion, substitution, deletion or addition of one to several amino acids in any one of the amino acid sequences of the antibody described in the above (4) and its CDRs, or an antibody having 1, 2, 3, 4, 5 or all of the CDRs of the antibody described in the above (4), as CDR(s); or an antigen-binding fragment thereof.

According to the present invention, there is provided an antibody that binds to TMEM132A or an antigen-binding fragment thereof, more specifically, (4a) an antibody comprising a heavy chain variable region having an amino acid sequence of a heavy chain variable region set forth in SEQ ID NO: 28 and a light chain variable region having an amino acid sequence of a light chain variable region set forth in SEQ ID NO: 32, an antibody that competes with the antibody described in the above (4a) for binding to TMEM132A, an antibody having an insertion, substitution, deletion or addition of one to several amino acids in any one of the amino acid sequences of the antibody described in the above (4a) and its CDRs, or an antibody having 1, 2, 3, 4, 5 or all of the CDRs of the antibody described in the above (4a), as CDR(s); or an antigen-binding fragment thereof.

According to the present invention, there is provided an antibody that binds to TMEM132A, or an antigen-binding fragment thereof, wherein the antibody binds to a part of an extracellular region of TMEM132A. In an embodiment of the present invention, the part of the extracellular region of TMEM132A, which is not particularly limited, may be, for example, the region at amino acid positions 143 to 317 or the region at amino acid positions 411 to 597 in GenBank Accession No.: NP_060340.

In the specification, the phrase "having an insertion, substitution, deletion or addition of one to several amino acids" means that any insertion, substitution, deletion or addition may be acceptable as long as the resultant antibody has a binding ability to TMEM132A. The phrase "having an insertion, substitution, deletion or addition of one to several amino acids" may mean having an insertion, substitution, deletion or addition of, for example, 1, 2, 3 or 4 amino acids. Substitution of an amino acid can be, for example, conservative substitution of an amino acid. Such an insertion, substitution, deletion or addition can be carried out by those skilled in the art by means of, e.g., a site-specific mutagenesis. Such an insertion, substitution, deletion or addition may be sometimes found also in a competitive antibody.

In the specification, the phrase "having an identity of 80% or more" means that, regarding the identity of the amino acid sequence of a target antibody with a reference antibody, when the two amino acid sequences is checked by aligning two amino acid sequences at a maximum correspondence rate, the number of amino acids in common is 80% or more relative to that of the reference. The above identity can be 80% or more, 85% or more, 90% or more, 95% or more, 98% or more and 99% or more. An antibody having "an identity of 80% or more" can be prepared by those skilled in the art by means of, e.g., site-specific mutagenesis. Such an insertion, substitution, deletion or addition is sometimes found also in a competitive antibody.

The antibody of the present invention can be obtained by using TMEM132A protein (for example, the amino acid sequence of human TMEM132A can be GenBank Accession No.: NP_060340) as an antigen in accordance with a method known to those skilled in the art. More specifically, an animal is immunized with an antigen and an adjuvant, and then, blood plasma is obtained from the immunized animal. In this manner, a polyclonal antibody can be obtained. Alternatively, an animal is immunized with an antigen and an adjuvant, and then, B lymphocytes are obtained from the immunized animal, fused with myeloma cells to form a hybridoma, which is further cloned to obtain a hybridoma producing a desire antibody.

A chimeric antibody can be produced by a method known in the art; for example, by replacing a constant region of an antibody with a constant region of a human antibody.

A humanized antibody contains, for example, a complementarity determining region (CDR) derived from non-human animal, a human antibody-derived framework region and a human antibody-derived constant region. A humanized antibody can be obtained, for example, by transplanting a non-human animal derived CDR as mentioned above to a human antibody. A human antibody can be obtained, for example, by immunizing a genetically modified mouse producing a human antibody with an antigen. A bispecific antibody is an antibody capable of binding to two different epitopes or antigens, and can be prepared by a method known to those skilled in the art. A bispecific antibody can be prepared by a method of fusing two types of cells producing different antibodies to form a hybrid hybridoma or by expressing a $V_H$ domain and $V_L$ domain on a single polypeptide chain via a short linker that cannot allow the two domains to form a pair and forming a complex with another polypeptide chain having a complementary $V_H$ domain and a $V_L$ domain making pairs with the above $V_H$ domain and $V_L$ domain.

An antibody which competes with a certain antibody in binding to an antigen can be obtained by, e.g., the competitive assay known to those skilled in the art. In the competitive assay, if an antibody can block binding of a desired antibody in a ratio of, for example, at least 20%, preferably at least 20 to 50% and further preferably at least 50%, the antibody can be an antibody that competes for binding to the same antigen. The competitive antibody can be identified by a cross-blocking assay, preferably, a competitive ELISA assay. In the cross-blocking assay, e.g., a microtiter plate is coated with an antigen. To the microtiter plate, a candidate competitive antibody is added and incubated to form a bond between the antigen and the candidate competitive antibody. Thereafter, a desired antibody, which has been labeled, is added to a well, incubated and washed to quantify the biding amount of the desired antibody. In this manner, whether the antibody competes or not can be determined. If the candidate antibody is a competitive antibody, the amount of the label remaining in the well should be lowered.

According to the present invention, TMEM132A is expressed in various cancer cells. TMEM132A is expressed particularly in epithelial cancer cells (for example, colorectal cancer cells, pancreatic cancer cells, ovarian cancer cells and breast cancer cells). In contrast, TMEM132A was not found in normal tissues. Thus, according to the present invention, there is provided a method for diagnosing cancer, comprising determining whether TMEM132A protein is present or not in a biological sample obtained from a subject. According to the present invention, there is also provided a method for detecting a cancer cell, comprising determining the presence or absence of TMEM132A protein in a biological sample obtained from a subject. According to the present invention, it is possible to determine the presence or absence of TMEM132A protein by means of an antibody that binds to TMEM132A. According to the present invention, it is possible determine the presence or absence of TMEM132A protein by using an antibody that binds to TMEM132A. The method for diagnosing cancer according to the present invention may further comprise applying a cancer treatment such as a chemotherapy and radiation therapy to a subject who has been diagnosed as having cancer.

According to the present invention, TMEM132A is expressed on the surface of cancer cells. According to the present invention, there is provided a conjugate of an antibody that binds to TMEM132A and a cytotoxic agent. The cytotoxic agent used in the present invention is, for example, a substance having an anticancer activity. The substance having an anticancer activity refers to a substance reducing the size of cancer, delaying or terminating growth of cancer, delaying or terminating proliferation of cancer cells, or inhibiting spreading cancer cells when the substance is brought into contact with cancer. Examples of the substance having an anticancer activity that can be used in the present invention include an anticancer agent, a toxin and a radioisotope. According to the present invention, there is also provided a pharmaceutical composition for use in treatment of cancer, containing a conjugate of an antibody that binds to TMEM132A and a cytotoxic agent. Examples of the cancer include an epithelial cancer (for example, colorectal cancer, pancreatic cancer, ovarian cancer and breast cancer).

In an embodiment of the present invention, the antibody of the present invention may have a cytotoxic activity such as antibody-dependent cellular cytotoxicity (ADCC activity) or complement-dependent cytotoxic activity (CDC activity). Particularly TMEM132A is preferable as a target of the antibody of the present invention, because TMEM132A is a protein expressed on the surface of cancer cells.

In order to enhance the ADCC activity of an antibody, a subtype of human antibody used in the constant region can be IgG1. In order to enhance the ADCC activity of an antibody, the antibody may, for example, include an antibody wherein one or more N-linked sugar chains bind to the Fc region of the antibody and wherein the reducing end of the N-linked sugar chain (N-acetylglucosamine) has no fucose bound thereto.

A pharmaceutical composition or drug containing the antibody of the present invention as an active ingredient can be formulated into a pharmaceutical preparation by a pharmaceutical preparation method known in the art. The pharmaceutical composition or drug of the present invention may contain, e.g., a pharmaceutically acceptable excipient. As the excipient, an excipient appropriately used for administering an effective amount of the antibody of the present invention serving as an active ingredient to a subject. In an embodiment, the pharmaceutical composition or drug of the present invention may be an injection. Examples of the excipient for an injection may include an aseptic aqueous solution, a pharmacological acceptable buffered solution, such as Ringer's solution, Hank's solution or physiological saline and an isotonic solution containing glucose and other additives. Examples of the additives that can be added in formulation of a pharmaceutical preparation include an alcohol such as ethanol, a polyalcohol such as polyethylene glycol and a nonionic surfactant such as polysorbate 80. Examples of an oily liquid that can be used for injection include sesame oil, coconut oil and soybean oil. As the additives, benzyl benzoate or benzyl alcohol can be used. The pharmaceutical composition or drug of the present invention can be parenterally administered (for example, intravenous administration or intrathoracic administration) in the form of an injection.

The ADCC activity or CDC activity of an antibody can be determined by a method known to those skilled in the art. The ADCC activity can be determined, for example, by incubating cancer cells and effector cells (for example, NK cells and monocytes) expressing an Fc acceptor in the presence of the antibody of the present invention under physiological conditions and counting the number of viable and/or dead cancer cells. The CDC activity can be determined, for example, by incubating cancer cells in a solution containing additives (for example, human serum) in the presence of the antibody under physiological conditions and counting the number of viable and/or dead cancer cells.

The cytotoxic activity can be enhanced by various methods known to those skilled in the art. For example, an antibody defective in sugar-chain fucose in an Fc region; an antibody having a sugar chain to which a bisecting N-acetylglucosamine (GlcNAc) is bound; and a method of strengthening the binding between an Fc acceptor of an effector cell and an antibody by amino acid substitution in the Fc region to enhance the cytotoxic activity are known. The antibody thus modified can be used as the antibody of the present invention.

For the purpose of, e.g., decreasing an antigenicity of an antibody itself in a human, the antibody can be modified by a method known to those skilled in the art into a genetically modified antibody such as a chimeric antibody, a humanized antibody or a human antibody. In the pharmaceutical composition or drug of the present invention, the antibody of the present invention may be a chimeric antibody, a humanized antibody or a human antibody. The antibody may be also a bispecific antibody.

According to the present invention, there is provided a conjugate of the antibody of the present invention or an antigen-binding fragment thereof and an imaging probe. According to the present invention, there is provided a composition, cancer diagnosis kit or cancer diagnostic agent for use in imaging cancer, containing the conjugate of the antibody of the present invention or an antigen-binding fragment thereof and an imaging probe. The composition, cancer diagnosis kit or cancer diagnostic agent for use in imaging cancer can be applied to epithelial cancer cells (for example, colorectal cancer cells, pancreatic cancer cells, ovarian cancer cells and breast cancer cells).

Examples of the imaging probe that can be used in the present invention include a fluorescence imaging probe, an enhancer such as a contrast medium (for example, paramagnetic ion) for nuclear magnetic resonance imaging (MRI), and a radioactive nuclide for imaging, such as PET molecular imaging probe.

According to the present invention, there is provide use of an antibody that binds to TMEM132A or an antigen-binding fragment thereof for producing a medicament for treating a cancer. According to the present invention, there is provided use of an antibody that binds to TMEM132A or an antigen-binding fragment thereof for manufacturing a composition, cancer diagnosis kit or cancer diagnosis agent for use in imaging cancer.

According to the present invention, there is provided a method for treating a cancer in a subject in need thereof, comprising administering an antibody that binds to TMEM132A to the subject. According to the present invention, there is also provided a method for treating a cancer in a subject in need thereof, comprising administering a conjugate of an antibody that binds to TMEM132A or an antigen-binding fragment thereof and a cytotoxic agent to the subject.

EXAMPLES

Example 1: Purification of TMEM132A Protein and Preparation of Monoclonal Antibody In this Example, in order to obtain an antibody against TMEM132A protein, TMEM132A protein was prepared and purified as an antigen.

1) Preparation of Antigen

A vector (ORIGENE RC214846) having TMEM132A gene integrated therein and the following primers were subjected to PCR amplification according to a routine method. As a DNA polymerase, PrimeStar HS DNA polymerase (R010A, Takara) was used. To the C terminal of each antigen, a tag sequence of 6×His was added.

Primer sequences for amplification of Immune antigen I
   catatgttccacctcaaagggcaggattg (SEQ ID NO: 33)
   gtcgaccttgaagcggtctagcttggcagtc (SEQ ID NO: 34)

Primer sequences for amplification of Immune antigen II
   catatgaatacagcaccactgactggagtg (SEQ ID NO: 35)
   gtcgacttccagagaggctacacgcgagtccag (SEQ ID NO: 36)

Immune antigen I herein corresponds to a part of the extracellular region of TMEM132A (the region of amino acid No. 143 to 317 of GenBank Accession No.: NP_060340); whereas, Immune antigen II corresponds to another part of the extracellular region of TMEM132A (the region of amino acid No. 411 to 597 of GenBank Accession No.: NP_060340)

Subsequently, the PCR amplification products obtained were each integrated into an expression vector pET21b. Specific procedure was as follows: each of pET21b and the PCR amplification product were reacted with NdeI and SalI (Takara) for two hours in accordance with the manufacturer protocol. Thereafter, the resultant cleaved DNA fragments were separated by 1% agarose gel electrophoresis, cut out from the gel and purified by promega wizard SV gal and PCR clean-up system kit.

The aforementioned expression vector and an insert containing immune antigen I or II were reacted with Ligation high (Toyobo Co., Ltd.) for 30 minutes.

Competent High DH5α (Toyobo Co., Ltd.) was transformed and cultured in an LB medium (50 µg/mL) plate. From the *Escherichia coli* transformed, a plasmid was extracted and subjected to sequencing to confirm that a desired gene was integrated into the vector.

Subsequently, an expression vector having the desired gene was transformed and introduced into *Escherichia coli* BL21 (DE3) for expressing a protein. Thereafter, BL21 (DE3) transformed was cloned.

BL21 (DE3) transformed was inoculated in 10 mL of LB medium and cultured at 37° C. for 16 hours. Then, the medium was exchanged with 1 L of LB medium and culture was carried out at 37° C. When the value at OD600 nm reached 0.6, IPTG was added so as to obtain a final concentration of 1 mM to induce gene expression and culture was carried out for further 4 hours.

Four hours later, *Escherichia coli* cells were crushed and the sediment was suspended in a denaturation buffer (50 mM Tris-HCl, 500 mM NaCl, 6M guanidine hydrochloride). After the buffer was allowed to permeate for 16 hours, the supernatant of the sample was collected and purified by a nickel column.

2) Preparation of Cell Line Forcibly Expressing TMEM132A

Plasmid pIRES2-AcGFP1 (Clontech) (0.5 Gg) having TMEM132A gene (Genbank Accession No.: NM_017870.3) and a Flag sequence incorporated therein was diluted with 0.1 mL of Opti-MEM (Invitrogen). To the dilution solution, Lipofectionamine LTX (2.5 µL) was added to prepare a solution for use in transfection. The solution was allowed to stand still at room temperature. Twenty five minutes later, the solution prepared above was added to a 24-well plate (Corning) containing DLD1 cells ($4 \times 10^4$ cells/well). After transfection, the cells were cultured in a medium supplemented with 0.5 mg/mL G418 (ThermoFisher) for 14 days. From the cultured cells, cells only expressing GFP were obtained by means of the FACSAria cell sorter (BD).

The cells obtained were subjected to limiting dilution and added in a 96-well plate. A well having a single colony was subjected to western blot. The cell confirmed to have a Flag sequence was determined as a forcible expression cell.

3) Preparation of Antibody

Immune antigen I or immune antigen II mentioned above was diluted with PBS to a concentration of 1 mg/mL and then mixed with Freund complete adjuvant in a ratio of 1:1 to prepare an emulsion. The emulsion (100 µL) was intraperitoneally administered to each of mice (Balb/c, female, 6 to 8 weeks old, Japan SLC). After that, the immune antigen mixed with an adjuvant (e.g., Gerbu adjuvant 100, Gerbu GmbH) was intraperitoneally administered at intervals of 14 days. Seven days after the third immunization, blood was obtained from 100 tail veins to prepare antiserum with PBS. The antibody titer of the serum was evaluated by ELISA using the immune antigen immobilized onto a solid phase or by flow cytometry of DLD-1 cells or K562 cells, and immunized mouse individuals for use in cell fusion was selected. To a mouse individual determined to have a sufficiently high antibody titer, an immune antigen diluted with PBS to a concentration of 1 µg/mL was administered to the abdominal cavity in an amount of 100 µL and to the tail vein in an amount of 400 µL as the final immunization. Three days after the final immunization, the spleen, iliac lymph node, inguinal lymph nodes, underarm lymph node and sub-knee lymph node were excised out and fused with mouse myeloma cells p3X63 by the PEG method. Ten to fourteen days after the fusion, the culture supernatant of the hybridoma cells were recovered. Antibody-producing hybridoma cells positive to DLD-1 cells, strong positive to DLD-1 cells forcibly expressing TMEM132A and negative to K562 cells were selected by flow cytometry. From the antibody-producing hybridoma cells selected, single clones were obtained (established) by the limiting dilution method. In this manner, T6-0429 clone, T6-1022 clone and T6-1179 clones were obtained from immune antigen II; and T6-1475 clone was obtained from immune antigen I. The monoclonal antibodies obtained from these clones are designated as T6-0429 antibody, T6-1022 antibody, T6-1179 antibody and T6-1475 antibody. The isotypes of the antibodies were determined by isotype-specific ELISA (Bethyl). T6-0429 antibody was specified as IgG2a, T6-1022 antibody as IgG2a, T6-1179 antibody as IgG1 and T6-1475 antibody as IgG2a.

Example 2: Cancer-Cell Recognition Ability of Monoclonal Antibody that Binds to TMEM132A In this Example, it was found that a monoclonal antibody that binds to TMEM132A does not react with normal tissues; however, it can recognize cancer cells.

Flow Cytometry

Cancer cells, i.e., a target to be measured, were suspended in a medium and added in a V-shape bottom 96-well plate (Corning) so as to contain $1 \times 10^5$ cells/well. The plate was centrifuged at a rate of 440×g and 4° C. for 3 minutes, and then, the supernatant was removed. To the cell pellet, the supernatant of antibody-producing hybridoma culture solution or antibody solution was added in a ratio of 50 µL/well to suspend the pellet. After a reaction was carried out at 4° C. for 45 minutes, washing was performed three times with 0.1% BSA/2 mM EDTA/PBS 200 µL/well. The supernatant was removed and a secondary antibody (50 µL/well) was added to the cell pellet to suspend the pallet. Note that, as the secondary antibody, AlexaFluor647 Goat anti-Rat IgG (H-L) (Life Technologies) was diluted 400 fold with 0.1% BSA/2 mM EDTA/PBS and put in use. After a reaction was carried out at 4° C. for 45 minutes, and then, washing was performed three times with 0.1% BSA/2 mM EDTA/PBS (200 µL/well). The supernatant was removed, and then, 1 µg/mL Propidium Iodide/0.1% BSA/2 mM EDTA/PBS (200 µL/well) was added to the cell pellet to suspend the cell pellet. The cells stained in this manner were measured by a flow cytometer such as Guava easyCyte 8HT (Merck Millipore) and the obtained data were analyzed by FlowJO (Tommy digital biology).

In the same manner as in the above flow cytometry, the cancer cell recognition ability of an antibody was checked by using human colorectal cancer cell line DLD-1 or TMEM132A forcibly expressing DLD-1 line or TMEM132A negative cell line K562 prepared in Example 1 and T6-0429 antibody. T6-0429 antibody was detected by an anti-mouse IgG antibody labeled with Alexa647. The results were as shown in FIG. 1.

As shown in FIG. 1, it was apparent that TMEM132A antibody, i.e., T6-0429 antibody, binds to DLD-1 line. It was also apparent that T6-0429 antibody bind to TMEM132A forcibly expressing DLD-1 line in a larger amount. Binding of T6-0429 antibody to K562 line was unable to be confirmed. From the results, it was demonstrated that colorectal cancer can be detected by TMEM132A. It was also found that TMEM1232A is expressed on the cancer cell membrane.

Next, it was shown that a monoclonal antibody that binds to TMEM132A detects colorectal cancer by means of a colorectal cancer tissue array.

In order to confirm that T6-0429 antibody can be used for immunohistochemical staining, first, immunochemical staining of DLD-1 line and TMEM132A forcibly expressing DLD-1 line with T6-0429 antibody was carried out.

First, cells were seeded in an appropriate amount on a chamber slide and incubated at 37° C. (overnight). The supernatant was removed and the wells were washed with DPBS, and thereafter, cold acetone was added (acetone fixation). The slide was allowed to stand still at room temperature for 10 minutes and washed three times with PBS-T and 3% $H_2O_2$ (prepared by diluting 30% $H_2O_2$ with ultra-pure water) was added. The slide was allowed to stand still at room temperature for 20 minutes and washed three times with PBS-T, and then, 5% skim milk-containing PBS-T was added. The slide was allowed to stand still at room temperature for 30 minutes, washed three times with PBS-T, and then, T6-0429 antibody (10 μg/mL) directly labeled with HRP was added. The slide was allowed to stand still at room temperature for one hour and washed three time with PBS-T and stained with DAB (allowed to stand still at room temperature for 5 minutes). The slide was washed with ultra-pure water, stained with hematoxylin (allowed to stand still at room temperature for 2 minutes), soaked in tap water and allowed to stand still for 10 minutes, further soaked in ethanol for 2 minutes×3 times and in xylene for 2 minutes×3 times, and then, dewatered, dried, enclosed by means of mount quick and dried. A stained image was observed by a microscope.

Figure 2:
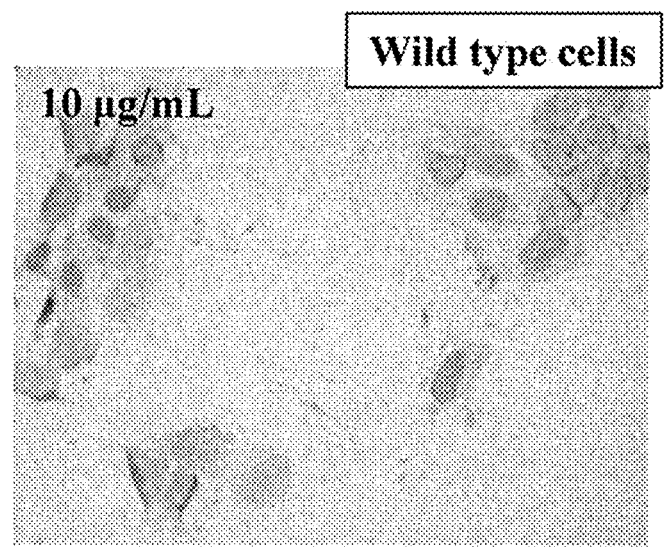
FIG. 2 shows that an anti-TMEM132A monoclonal antibody newly obtained can stain DLD-1 line in which TMEM132A protein was forcibly expressed.
Figure 2:
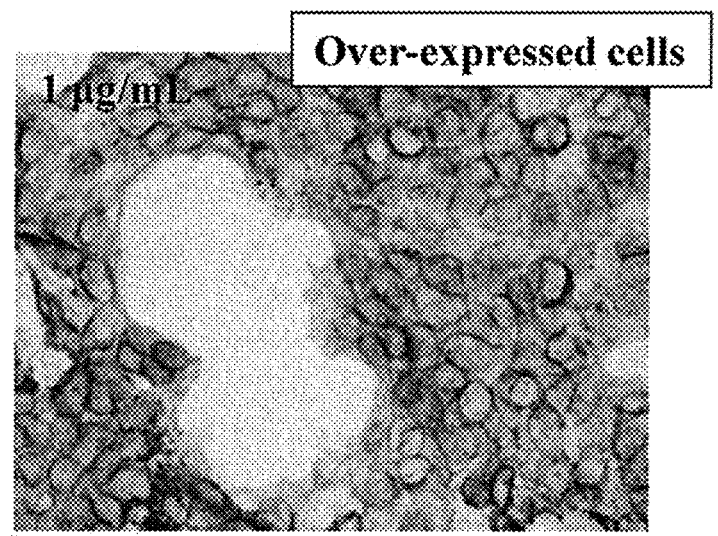
Figure 2:
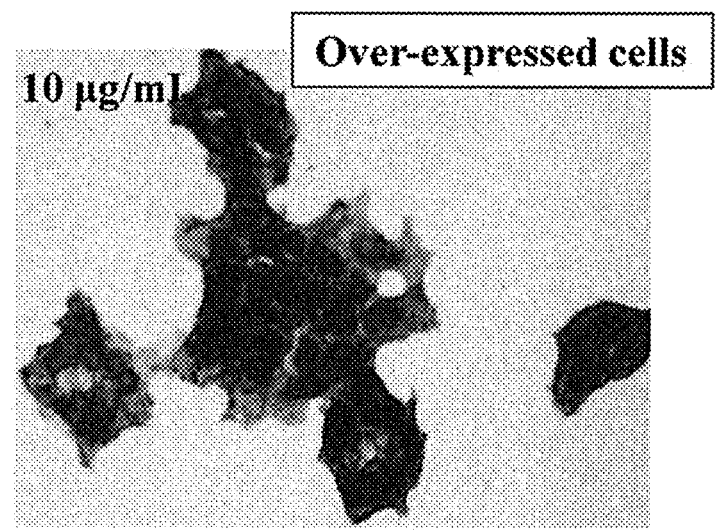

The results were as shown in FIG. 2. As shown in FIG. 2, human colorectal cancer cell line DLD-1 was positive to T6-0429 antibody. TMEM132A forcibly expressing DLD-1 line strongly expressed TMEM132A and showed a strong positive reaction to T6-0429 antibody.

Figure 3:
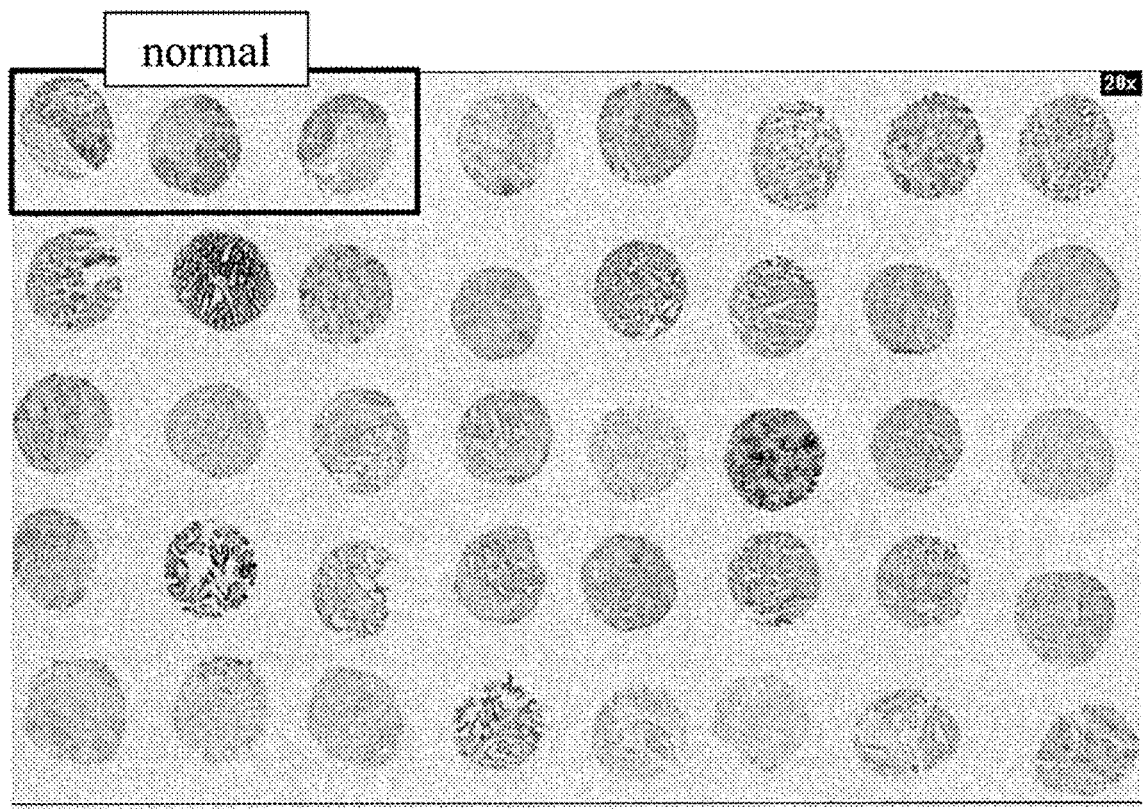
FIG. 3 shows the results of staining a colorectal cancer tissue panel with an anti-TMEM132A monoclonal antibody.
Figure 4:
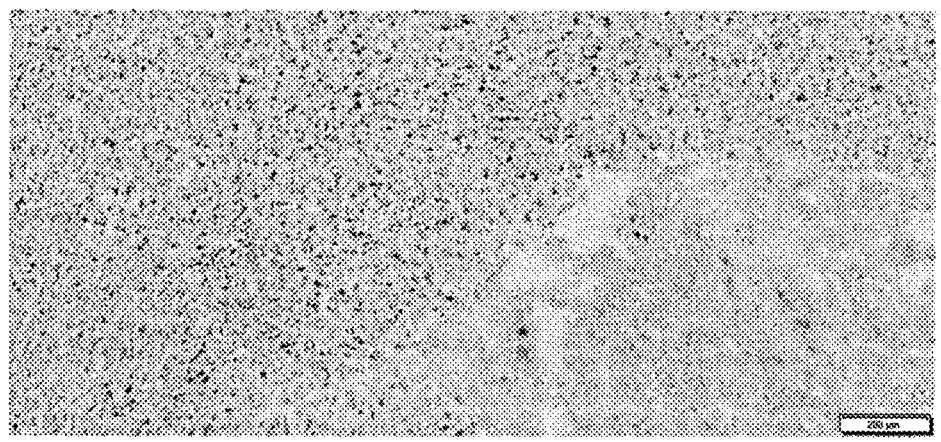
FIG. 4 shows the results of staining a normal brain tissue and a normal cardiac tissue with an anti-TMEM132A monoclonal antibody.
Figure 4:
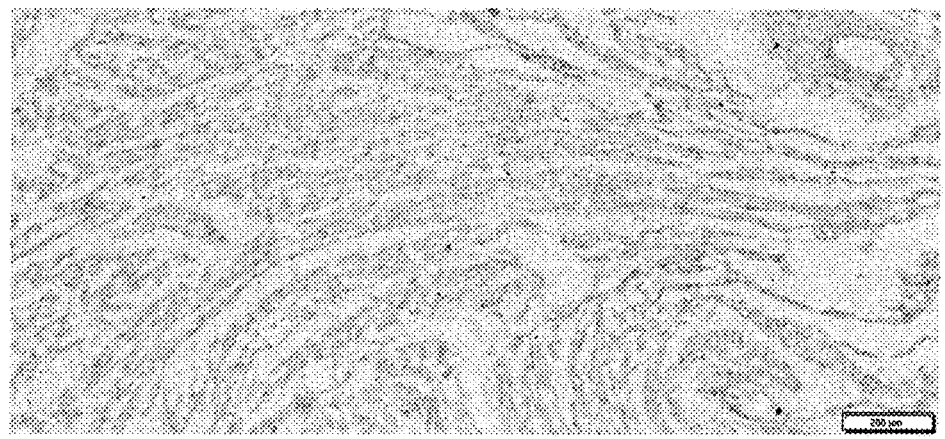
Figure 5:
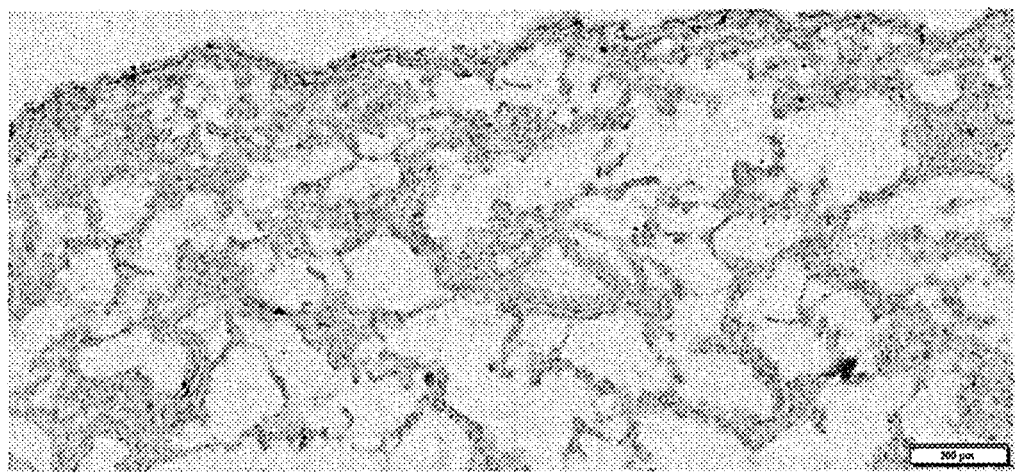
FIG. 5 shows the results of staining a normal lung tissue and a normal liver tissue with an anti-TMEM132A monoclonal antibody.
Figure 5:
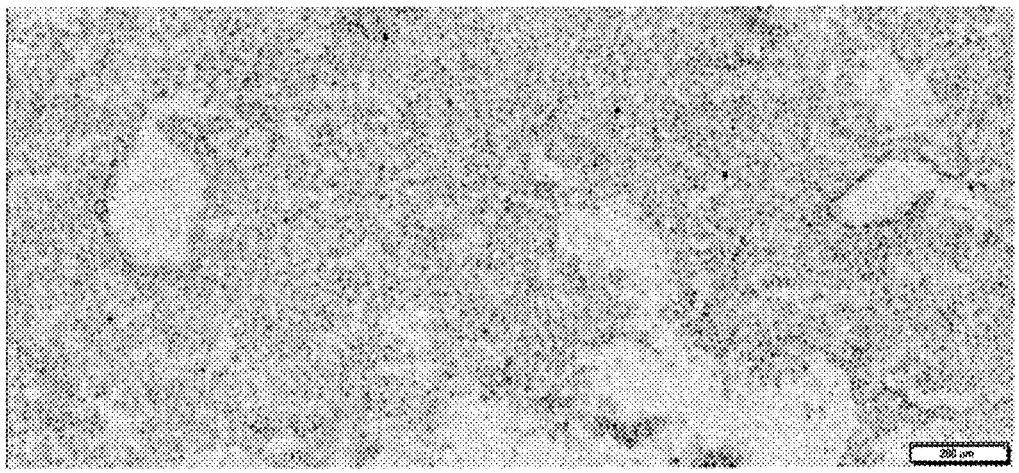
Figure 6:
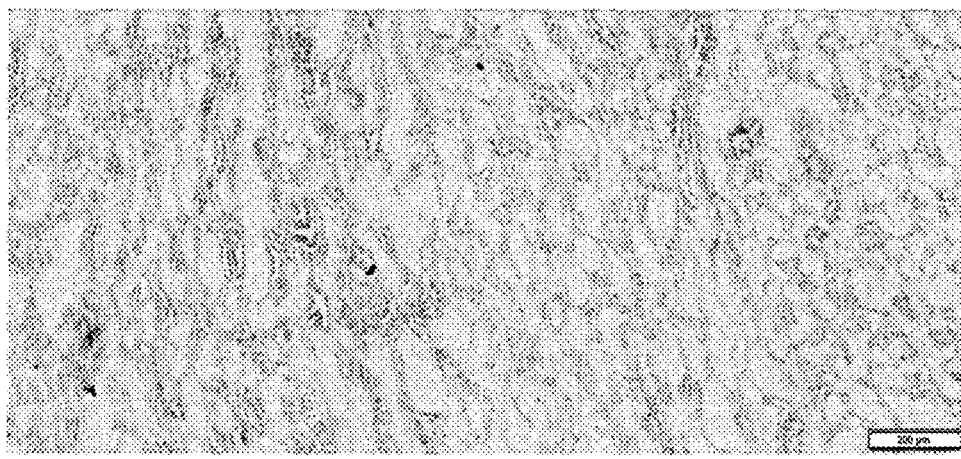
FIG. 6 shows the results of staining normal kidney tissue and a normal small intestine tissue with an anti-TMEM132A monoclonal antibody.
Figure 6:
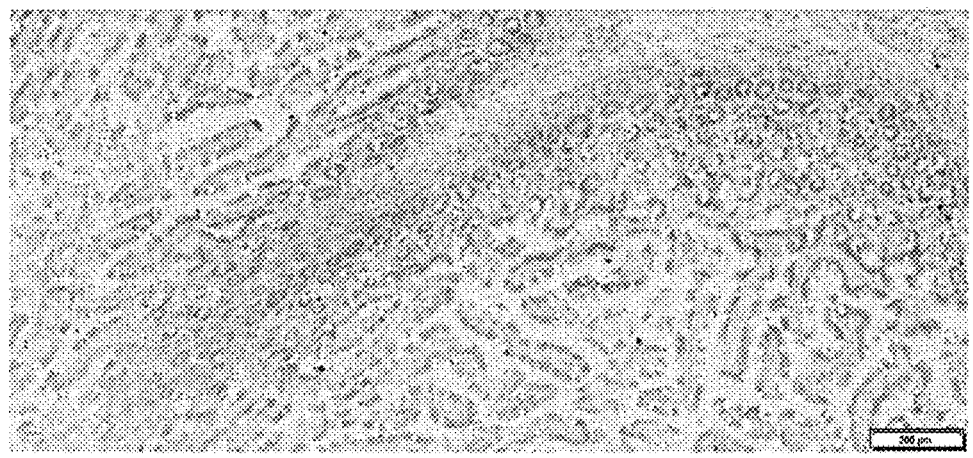
Figure 7:
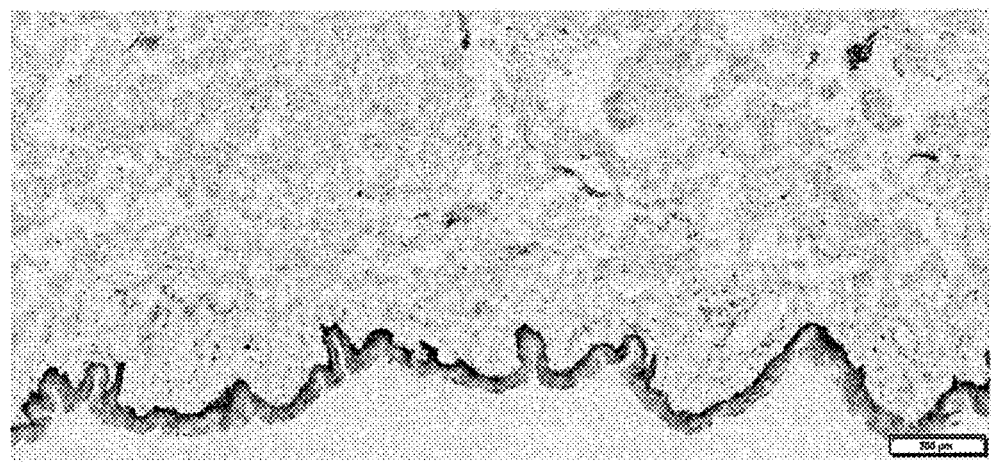
FIG. 7 shows the results of staining normal skin with an anti-TMEM132A monoclonal antibody.

The colorectal cancer tissue arrays were obtained from BioChain Institute Inc. (Newark, Calif.) and used in experiments. Each tissue array was stained in accordance with the manufacturer's manual. As the antibody, T6-0429 antibody (10 μg/mL) was used. The results were as shown in FIG. 3. As shown in FIG. 3, the stained images of normal colon tissues with T6-0429 antibody were not detectable; however, about 30% of the colorectal cancer tissues was positive to T6-0429 antibody. From the results, it was shown that an antibody that binds to TMEM132A can detect colorectal cancer. A breast cancer tissue array was obtained from BioChain Institute Inc. (Newark, Calif.) and checked in the same manner. As a result, it was found that about 20% is positive. From this fact, an antibody that binds to TMEM132A can detect breast cancer.

It was further checked whether a normal tissue can be recognized by T6-0429 antibody (10 μg/mL). Paraffin slices of a normal tissue specimen were prepared in accordance with a routine method and subjected to immunohistochemical staining using T6-0429 antibody (10 μg/mL). The procedure is more specifically as follows. Thin-sliced samples or cryopreserved samples were air-dried (at room temperature, for about 30 minutes). Cold acetone was added to the samples, which were allowed to stand still at room temperature for 10 minutes (acetone fixation). After the samples were washed three times with PBS-T, 3% $H_2O_2$ (prepared by diluting 30% $H_2O_2$ with ultra-pure water) was added to the samples, which were allowed to stand still at room temperature for 20 minutes. After the samples were washed three times with PBS-T, 5% skim milk-containing PBS-T were added to the samples, which were allowed to stand still at room temperature for 30 minutes. After the samples were washed three times with PBS-T, T6-0429 antibody (10 μg/mL) directly labeled with HRP was added to the samples, which were allowed to stand still at room temperature for one hour. After the samples were washed three times with PBS-T, the samples were stained with DAB (allowed to stand still at room temperature for 5 minutes). The samples were washed with ultra-pure water, and then, stained with hematoxylin in accordance with a routine method (allowed to stand still at room temperature for 2 minutes), soaked in tap water, allowed to stand still for 10 minutes, further soaked in ethanol for 2 minutes×3 times and in xylene for 2 minutes×3 times, and then, allowed to penetrate and dewatered, enclosed by means of Mount-Quick and dried. Stained images were observed by a microscope.

The results were as shown in FIGS. 4 to 7. As shown in FIGS. 4 to 7, T6-0429 antibody was negative in any one of the normal tissues of the skin, brain, small intestine, liver, heart, lung and kidney. However, a positive site was limitedly found in the normal skin tissue (see FIG. 7).

Using an anti-TMEM132A antibody, detection of various epithelial cancer cell lines was made by FACS.

More specifically, cancer cells to be measured were suspended in a medium and added to a V-shape bottom 96-well plate (Corning) so as to contain $1 \times 10^5$ cells/well. The plate was centrifuged at a rate of 440×g and 4° C. for 3 minutes, and then, the supernatant was removed. To the cell pellet, the supernatant of antibody-producing hybridoma culture solution or antibody solution was added in a ratio of 50 μL/well to suspend the pellet. After a reaction was carried out on ice for 45 minutes, washing was performed three times with 0.1% BSA/2 mM EDTA/PBS 200 μL/well. The supernatant was removed and a secondary antibody (50 μL/well) was added to the cell pellet to suspend the pellet. Note that, as the secondary antibody, AlexaFluor647 Goat anti-Rat IgG (H-L) (Life Technologies) was diluted 400 fold with 0.1% BSA/2 mM EDTA/PBS and put in use. After a reaction was carried out on ice for 45 minutes, washing was performed three times with 0.1% BSA/2 mM EDTA/PBS 200 μL/well. The supernatant was removed, and then, 50 ng/mL Propidium Iodide/0.1% BSA/2 mM EDTA/PBS (250 μL/well) was added to the cell pellet to suspend the pellet. The cells stained in this manner were measured by a flow cytometer such as Guava easyCyte 8HT (Merck Millipore) and the obtained data was analyzed by FlowJO (Tommy digital biology).

As the cancer cell lines, a breast cancer cell line, a colorectal cancer cell line, an ovarian cancer cell line and a pancreatic cancer cell line were used.

The results were as shown in the following Table 1.

[Table 1]

TABLE 1

Expression of TMEM132A on cell surface of cancer cell lines

| Origin of cell line | Number of positive lines/Number of all lines |
|---|---|
| Breast cancer cell line | 2/4 |
| Colorectal cancer cell line | 7/7 |
| Ovarian cancer cell line | 3/5 |
| Pancreatic cancer cell line | 10/10 (reaction of 3 cells is more than the reaction of Herceptin |

As shown in Table 1, it was found in FACS analysis that TMEM132A is widely expressed on the surface of cancer cells such as a breast cancer cell line, a colorectal cancer cell line, an ovarian cancer cell line and a pancreatic cancer cell line.

From the result, it was demonstrated that anti-TMEM132A antibody is useful for cancer detection. It was also suggested that giving ADCC activity or CDC activity to the anti-TMEM132A antibody (for example, by converting the isotype of the antibody to isoform having high ADCC activity, such as IgG1 and IgG3) is useful for cancer treatment.

Example 3: Sequence Determination of Monoclonal Antibody

In this Example, the sequences of a heavy chain variable region and light chain variable region of a monoclonal antibody were determined.

Total RNAs were extracted from T6-0429 clone, T6-1022 clone, T6-1179 clone and T6-1475 clone obtained in Example 1 by means of RNeasy Mini Kit (QIAGEN). From each of the total RNAs, cDNA was synthesized by means of SMARTer RACE 5'/3'Kit (Takara) in accordance with 5' end RACE (rapid amplification of cDNA ends) method.

Using the cDNA obtained as a template and KOD FX Neo (manufactured by Toyobo Co., Ltd.), a desired gene was amplified. The amplification conditions were: 5 cycles, each consisting of a denaturation step at 98° C. for 10 seconds, an annealing step at 68° C. for 30 seconds and an extension step at 72° C. for 90 seconds; 5 cycles each consisting of a denaturation step at 98° C. for 10 seconds, an annealing step at 65° C. for 30 seconds and an extension step at 68° C. for 90 seconds; and 25 cycles, each consisting of a denaturation step at 98° C. for 10 seconds, an annealing step at 63° C. for 30 seconds and an extension step at 68° C. for 90 seconds and a touchdown PCR method was employed. PCR was carried out by using a PCR apparatus (Applied Biosystem ProFlex PCR System).

In the PCR, the following primer sequences were used.

```
Forward primer for heavy chain:
                                      (SEQ ID NO: 37)
CTAATACGACTCACTATAGGGCAAGCAGTGGTATCAACGCAGAGT
or
                                      (SEQ ID NO: 38)
CTAATACGACTCACTATAGGGC Reverse primer for heavy chain:
                                      (SEQ ID NO: 39)
CCCATGGCCACCARATTCTYATCAGACAG Forward primer for light chain:
                                      (SEQ ID NO: 40)
CTAATACGACTCACTATAGGGCAAGCAGTGGTATCAACGCAGAGT (SEQ ID NO: 41)
CTAATACGACTCACTATAGGGC Reverse primer for light chain:
                                      (SEQ ID NO: 42)
GTTGTTCAWGARGCACACGACTGAGGCA
```

The PCR products of H chain and L chain amplified, were subjected to TA cloning by means of Target Clone—plus- (manufactured by Toyobo Co., Ltd.). After cloning, DH5α (manufactured by Toyobo Co., Ltd.) was transformed. From a single colony, a plasmid was extracted by means of Plasmid Mini Kit (QIAGEN). The genes of H chain and L chain cloned were subjected to analysis of nucleotide sequence using ABI PRISM 3100 Genetic Analyzer. The results were as shown in the following Tables. In the heavy chain variable regions, a region of amino acid No. 1 to 19 was a signal sequence. In the light chain variable regions, a region of amino acid No. 1 to 20 was a signal sequence. However, in the heavy chain variable region of T6-1475 clone, a region of amino acid No. 1 to 18 was a signal sequence.

Heavy Chain Variable Region (SEQ ID NO: 4) of T6-0429 Clone

CDR1: SEQ ID NO: 1, CDR2: SEQ ID NO: 2, CDR3: SEQ ID NO: 3

[Formula 1]

```
  1 ATG AAC TTC GGG CTC AGC TTG ATT TTC CTT GTC CTT ATT TTA AAA GGT GTC CAG TGT GAA   60
    M   N   F   G   L   S   L   I   F   L   V   L   I   L   K   G   V   Q   C   E

61 GTG CAG CTC GTG GAG TCT GGG GSA GGC TTA GTG AGG CCT GGA GGG TCC CTG AAA CTC TCC  120
    V   Q   L   V   E   S   G   G   G   L   V   R   P   G   G   S   L   K   L   S

CDR1
121 TGT GCA GCC TCT GGA TTC ACT TTC AGT AAC TAT GCC ATG TCT TGG GTT CGC CAG TCT CCA  180
    C   A   A   S   G   F   T   F   S   N   Y   A   M   S   W   V   R   Q   S   P

CDR2
181 GAG AAG AGG CTG GAA TGG GTC GCA GAA GTC AGT TAT GGT GGT AGT TAC ACC TAC TAT TCA  240
    E   K   R   L   E   W   V   A   E   V   S   Y   G   G   S   Y   T   Y   Y   S

241 GAC ACT GTG ACG GGC CGA TTC ACC ATC TCC AGA GAC AAT GCC AAG AAC ACC CTG TAC CTG  300
    D   T   V   T   G   R   F   T   I   S   R   D   N   A   K   N   T   L   Y   L

CDR3
301 GAC ATG AGC ACT CTG AGG TCT GAG GAC TCG GCC ATG TAT TAC TGT GTG AGG TGT GGA AGT  360
    D   M   S   L   R   S   E   D   S   A   I   Y   Y   C   V   R   C   G   S

361 AAC TCA GCC TGG TTT GGT TTC TGG GGC CAA GGG ACT CTG GTC ACT GTC TCT            411
    N   S   A   W   F   G   F   W   G   Q   G   T   L   V   T   V   S
```

Light Chain Variable Region (SEQ ID NO: 8) of T6-0429 Clone
 CDR1: SEQ ID NO: 5, CDR2: SEQ ID NO: 6, CDR3: SEQ ID NO: 7

[Formula 2]

```
  1  ATG ATG AGT CCT GCC CAG TTC CTG TTT CTG TTA GTG CTC TGG ATT CAG GAA ACC AAG GGT   60
      M   M   S   P   A   Q   F   L   F   L   L   V   L   W   I   Q   E   T   K   G

61  GAT GTT GTG ATG ACC CAG ACT CCA CTC ACC TTG TCG GTT ACC ATT GGA CAA CCA GCC TCT  120
      D   V   V   M   T   Q   T   P   L   T   L   S   V   T   I   G   Q   P   A   S

CDR1
121  ATC TCT TGC|AAG TCA AGT CAG AGC CTC TTA TCT AAT AAT GGA AAA ACC TAT TTG AAT|TGG  180
      I   S   C | K   S   S   Q   S   L   L   S   N   N   G   K   T   Y   L   N | W

CDR2
181  TTA TTA CAG AGG CCA GGC CAG TCT CCA AAG CGC CTA ATT TAT|CTG GTA TCT GAA CTG GAC| 240
      L   L   Q   R   P   G   Q   S   P   K   R   L   I   Y | L   V   S   E   L   D |

241  |TCT|GGA GTC CCT GAC AGG TTC AGT GGC AGT GGA TCA GGA ACA GAT TTT ACA CTG AAA ATC  300
     | S |  G   V   P   D   R   F   S   G   S   G   S   G   T   D   F   T   L   K   I

CDR3
301  AGC AGA GTG GAG GCT GAG GAT TTG GGA GTT TAT TAC TGC|GTG CAA GGT ACA CAT TTT CCG| 360
      S   R   V   E   A   E   D   L   G   V   Y   Y   C | V   Q   G   T   H   F   P |

361  |TAC ACG|TTC GGA GGG GGG ACC AAA CTG GAA ATA AAA                                  396
     | Y   T | F   G   G   G   T   K   L   E   T   K
```

Heavy Chain Variable Region (SEQ ID NO: 12) of T6-1022 Clone
 CDR1: SEQ ID NO: 9, CDR2: SEQ ID NO: 10, CDR3: SEQ ID NO: 11

[Formula 3]

```
  1  ATG AAC CTC GGG CTC AGC CTG ATT TTC CTT GTC CTT ATT TTA AAA GGT GTC CAG TGT GAA   60
      M   N   L   G   L   S   L   I   F   L   V   L   I   L   K   G   V   Q   C   E

61  GTG CAG CTG GTG GAA TCT GGG GGA GGC TTA GTG AAG CCT GGA GGG TCC CTG AAA CTC TCC  120
      V   Q   L   V   E   S   G   G   G   L   V   K   P   G   G   S   L   K   L   S

CDR1
121  TGT GCA GCC TCT GGA TTC ACT TTC AGT|AGC TAT GCC ATG TCT|TGG GTT CGC CAG TCT CCA  160
      C   A   A   S   G   F   T   F   S | S   Y   A   M   S | W   V   R   Q   S   P

CDR2
161  GAG AAG AGG CTG GAG TGG GTC GCA|GAA ATC AGT TAT GGT GGT AGT TTT ACC TAC TAT CCA| 240
      E   K   R   L   E   W   V   A | E   I   S   Y   G   G   S   F   T   Y   Y   P |

241  |GAC ACT GTG ACG|GGC CGA TTC ACC ATC TCC AGA GAC AAT GTC AAG AAT ATC CTG TAC CTG  300
     | D   T   V   T | G   R   F   T   I   S   R   D   N   V   K   N   I   L   Y   L

CDR3
301  GAA ATG AGC AGT CTG ATG TCT GAG GAC ACG GCC ATG TAT TAC TGT GTA AGG|GCT GGA AGT| 360
      E   M   S   S   L   M   S   E   D   T   A   M   Y   Y   C   V   R | A   G   S |

361  |AAC TCA GCC TGG TTA AGT TAC|TCC GGC CAA GGG ACT CTG GTC ACT GTC TCT             411
     | N   S   A   W   L   S   Y | W   G   Q   G   T   L   V   T   V   S
```

Light Chain Variable Region (SEQ ID NO: 16) of T6-1022 Clone
CDR1: SEQ ID NO: 13, CDR2: SEQ ID NO: 14, CDR3: SEQ ID NO: 15

[Formula 4]

```
  1  ATG ATG AGT CCT GCC CAG TTC CTG TTT CTG TTA GTG CTC TGG ATT CAG GAA ACC AAC GGT   60
      M   M   S   P   A   Q   F   L   F   L   L   V   L   W   I   Q   E   T   N   G

61  GAT GTT GTG ATG ACC CAG ACT CCA CTC ACT TTG TCG GTT ACC ATT GGA CAA CCA GCC TCT  120
      D   V   V   M   T   Q   T   P   L   T   L   S   V   T   I   G   Q   P   A   S

CDR1
121  ATC TCT TGC|AAG TCA AGT CAG AGC CTC TTA TCT AGT AAT GGA AAA GCC TAT TTG AAT|TGG  180
      I   S   C | K   S   S   Q   S   L   L   S   S   N   G   K   A   Y   L   N | W

CDR2
161  TTA TTA CAG AGG CCA GGC CAG TCT CCA AAG CGC CTA ATC TAT|CTG GTG TCT GAA CTG GAC| 240
      L   L   Q   R   P   G   Q   S   P   K   R   L   I   Y | L   V   S   E   L   D |

241  |TCT|GGA GTC CCT GAC AGG TTC ACT GGC AGT GGA TCG GGA ACA GGA TTT ACA CTG AAA ATC  300
      | S |  G   V   P   D   R   F   T   G   S   G   S   G   T   G   F   T   L   K   I

CDR3
301  AGC AGA GTG GAG GCT GAG GAT TTG GGA ATT TAT TAC TGC|GTT CAA GGT ACA CAT TTT CCG  360
      S   R   V   E   A   E   D   L   G   I   Y   Y   C | V   Q   G   T   H   F   P

361  |TAC ACG|TTC GGA GGG GGG ACC AAG CTG GAA ATA AAA                                  396
      | Y   T | F   G   G   G   T   K   L   E   I   K
```

Heavy Chain Variable Region (SEQ ID NO: 20) of T6-1179 Clone
CDR1: SEQ ID NO: 17, CDR2: SEQ ID NO: 18, CDR3: SEQ ID NO: 19

[Formula 5]

```
  1  ATG AAC TTC GGG CTC AGC TTG ATT TTC CTT GTC CTT ATT TTA AAA GGT GTC CAG TGT GAA   60
      M   N   F   G   L   S   L   I   F   L   V   L   I   L   K   G   V   Q   C   E

61  GTG CAG CTG GTG GAG TCT GGG GGA GGC TTA GTG AAG CCT GGA GGG TCC CTG AAA CTC TCC  120
      V   Q   L   V   E   S   G   G   G   L   V   K   P   G   G   S   L   K   L   S

CDR1
121  TGT GCA GCC TCT GGA TTC ACT TTC AGT|AGC TCT GCC ATG TCT|TGG GTT CGC CAG TCT CCA  180
      C   A   A   S   G   F   T   F   S | S   S   A   M   S | W   V   R   Q   S   P

CDR2
181  GAG AAG AGG CTG GAA TGG GTC GGA|GAA ATT AGT TAT GGT GGT AGT TAC ACT TAC TAT CCA  240
      E   K   R   L   E   W   V   G | E   I   S   Y   G   G   S   Y   T   Y   Y   P

241  |GAC ACT GTG ACG|GGC CGA TTC ACC ATC TCC AGA GAC AAT GCC AAG AAC ACC CTG TAC CTG  300
      | D   T   V   T | G   R   F   T   I   S   R   D   N   A   K   N   T   L   Y   L

CDR3
301  GAA ATG AGC AGT CTG AGG TCT GAG GAC ACG GCC ATG TAT TAC TGT GTA AGG|GGT GGA AGT  360
      E   M   S   S   L   R   S   E   D   T   A   M   Y   Y   C   V   R | G   G   S

361  |AAC TCA GCC TGG TTT GCT TAC|TGG GGC CAA GGG ACT CTG GTC ACT GTC TCT           411
      | N   S   A   W   F   A   Y | W   G   Q   G   T   L   V   T   V   S
```

Light Chain Variable Region (SEQ ID NO: 24) of T6-1179 Clone
CDR1: SEQ ID NO: 21, CDR2: SEQ ID NO: 22, CDR3: SEQ ID NO: 23

[Formula 6]

```
  1  ATG ATG AGT CCT GCC CAG TTC CTG TCT CTG TTA GTG CTC TGG ATT CAG GAA ACC AAC GGT   60
      M   M   S   P   A   Q   P   L   S   L   L   V   L   W   I   Q   E   T   N   G

61  GAT GTT GTG ATG ACC CAG ACT CCA CTC ACT TTG TCG GTT ACC ATT GGA CAA CCA GCC TCT  120
      D   V   V   M   T   Q   T   P   L   T   L   S   V   T   I   G   Q   P   A   S

CDR1
121  ATC ACT TGC|AAG TCA AGT CAG AGA CTC TTA TAT AGT AAT GGA AAA ACC TAT TTG AAT|TGG  180
      I   T   C | K   S   S   Q   R   L   L   Y   S   N   G   K   T   Y   L   N | W

CDR2
181  TTA CTA CAG AGG CCA GGC CAG TCT CCA AAG CGC CTA ATT TAT|CTG GTG TCT AAA CTG GAC  240
      L   L   Q   R   P   G   Q   S   P   K   R   L   I   Y | L   V   S   K   L   D

241  |TCT|GGA GTC CCT AAC AGG TTC ACT GAC AGT GGA TCA GGA ACA GAT TTT ACA CTG AAA ATC  300
      | S | G   V   P   N   R   F   T   D   S   G   S   G   T   D   F   T   L   K   I

CDR3
301  AGC AGA GTG GAG GCT GAG GAT TTG GGA GTT TAT TAC TGC|GTA CAA GGT ACA CAT TTT CCG  360
      S   R   V   E   A   E   D   L   G   V   Y   Y   C | V   Q   G   T   H   F   P

361  |TAC ACG|TTC GGA GGG GGG ACC AAG CTG GAA ATA AAA                                   396
      | Y   T | F   G   G   G   T   K   L   E   I   K
```

Heavy Chain Variable Region (SEQ ID NO: 28) of T6-1475 Clone
CDR1: SEQ ID NO: 25, CDR2: SEQ ID NO: 26, CDR3: SEQ ID NO: 27

[Formula 7]

```
  1  ATG AAA GTG TTG AGT CTG TTG TAC CTG TTG ACA GCC ATT CCT GGT GCC CTG TCT GAT GTA   60
      M   K   V   L   S   L   L   Y   L   L   T   A   I   P   G   A   L   S   D   V

61  CAG CTT CAG GAG TCA GGA CCT GGC CTC GTG AAA CCT TCT CAG TCT CTG TCT CTC ACC TGC  120
      Q   L   Q   E   S   G   P   G   L   V   K   P   S   Q   S   L   S   L   T   C

CDR1
121  TCT GTC ACT GGC TAC TCC ATC ACC|AGT GAT TAT TAC TGG AAC|TGG ATC CGG CAG TTT CCT  180
      S   V   T   G   Y   S   I   T | S   D   Y   Y   W   N | W   I   R   Q   F   P

CDR2
181  GGA AAC AAA CTG GAA TGG ATG GGC|TAC ATT AGG TAC GAC GGT TAC AAT GCC TAC AAT CCA  240
      G   N   K   L   E   W   M   G | Y   I   R   Y   D   G   Y   N   A   Y   N   P

241  |TCT CTC AAA|AGT CGA ATT TCC ATC ACT CGT GAC ACA TCT AAG AAC CAG TTT TTA CTG AAG  300
      | S   L   K | S   R   I   S   I   T   R   D   T   S   K   N   Q   F   L   L   K

CDR3
301  TTG AAG TCT GTG ACT ACT GAG GAC ACA GCT ACA TAT TTC TGT GCA AGA|AAT GAT TAC GAC  360
      L   K   S   V   T   T   E   D   T   A   T   Y   F   C   A   R | N   D   Y   D

361  |GGG TAC TAC TTT GAC AAC|TGG GGC CAA GGC ACC ACT CTC ACA GTC TCC                  408
      | G   Y   Y   F   D   N | W   G   Q   G   T   T   L   T   V   S
```

Light Chain Variable Region (SEQ ID NO: 32) of T6-1475 Clone
CDR1: SEQ ID NO: 29, CDR2: SEQ ID NO: 30, CDR3: SEQ ID NO: 31

[Formula 8]

```
  1  ATG GAT TCA CAG GCC CAG GTT CTT ATG TTA CTG CTG CTA TGG GTA TCT GGT ACC TGT GGG   60
      M   D   S   Q   A   Q   V   L   M   L   L   L   L   W   V   S   G   T   C   G

61  GAC ATT GTG ATG TCA CAG TCT CCA TCC TCC CTA GCT GTG TCA GTT GGA GAG AAG GTT ACT  120
      D   I   V   M   S   Q   S   P   S   S   L   A   V   S   V   G   E   K   V   T

CDR1
121  ATG AGC TGC AAG TCC AGT CAG AGC CTT TTA TAT AGT ACC AAT CAA AAG AAC TAC TGG GCC  180
      M   S   C   K   S   S   Q   S   L   L   Y   S   T   N   Q   K   N   Y   L   A

CDR2
181  TGG TAC CAG CAG AAA CCA GGG CAG TCT CCT CAA CTG CTG ATT TAC TGG GCA TCC ACT AGG  240
      W   Y   Q   Q   K   P   G   Q   S   P   Q   L   L   I   Y   W   A   S   T   R

241  GAA TCT GGG GTC CCT GAT CGC TTC ACA GGC AGT GGA TCT GGG ACA GAT TTC ACT CTC ACC  300
      E   S   G   V   P   D   R   F   T   G   S   G   S   G   T   D   F   T   L   T

CDR3
301  ATC AGC AGT GTG AGC GCT GAA GAC CTG GCA GTT TAT TAC TGT CAG CAA TAT TAT ACC AAC  360
      I   S   S   V   S   A   E   D   L   A   V   Y   Y   C   Q   Q   Y   Y   T   N

361  CCG TAC ACG TTC GGA GGG GGG GCC AAG CTG GAA ATA AAA                              399
      P   Y   T   F   G   G   G   A   K   L   E   I   K
```

The sequence list describes the following sequences.

TABLE 2

| SEQ ID No. | Content of Sequence |
|---|---|
| SEQ ID Nos. 1-3 | Heavy chain CDRs 1 to 3 of T6-0429 clone |
| SEQ ID No. 4 | Heavy chain variable region of T6-0429 clone |
| SEQ ID Nos. 5-7 | Light chain CDRs 1 to 3 of T6-0429 clone |
| SEQ ID No. 8 | Light chain variable region of T6-0429 clone |
| SEQ ID Nos. 9-11 | Heavy chain CDRs 1 to 3 of T6-1022 clone |
| SEQ ID No. 12 | Heavy chain variable region of T6-1022 clone |
| SEQ ID Nos. 13-15 | Light chain CDRs 1 to 3 of T6-1022 clone |
| SEQ ID No. 16 | Light chain variable region of T6-1022 clone |
| SEQ ID Nos. 17-19 | Heavy chain CDRs 1 to 3 of T6-1179 clone |
| SEQ ID No. 20 | Heavy chain variable region of T6-1179 clone |
| SEQ ID Nos. 21-23 | Light chain CDRs 1 to 3 of T6-1179 clone |

TABLE 2-continued

| SEQ ID No. | Content of Sequence |
|---|---|
| SEQ ID No. 24 | Light chain variable region of T6-1179 clone |
| SEQ ID Nos. 25-27 | Heavy chain CDRs 1 to 3 of T6-1475 clone |
| SEQ ID No. 28 | Heavy chain variable region of T6-1475 clone |
| SEQ ID Nos. 29-31 | Light chain CDRs 1 to 3 of T6-1475 clone |
| SEQ ID No. 32 | Light chain variable region of T6-1475 clone |
| SEQ ID No. 33 | Forward primer for amplification of Immune antigen I |
| SEQ ID No. 34 | Reverse primer for amplification of Immune antigen I |
| SEQ ID No. 35 | Forward primer for amplification of Immune antigen II |
| SEQ ID No. 36 | Reverse primer for amplification of Immune antigen II |
| SEQ ID No. 37 | Forward primer 1 for heavy chain |
| SEQ ID No. 38 | Forward primer 2 for heavy chain |
| SEQ ID No. 39 | Reverse primer for heavy chain |
| SEQ ID No. 40 | Forward primer 1 for light chain |
| SEQ ID No. 41 | Forward primer 2 for light chain |
| SEQ ID No. 42 | Reverse primer for light chain |

The invention claimed is:

1. An antibody that binds to TMEM132A, or an antigen-binding fragment thereof, wherein the antibody is selected from the group consisting of:

(1) an antibody comprising a heavy chain variable region comprising a heavy chain CDR1 having an amino acid sequence set forth in SEQ ID NO: 1, a heavy chain CDR2 having an amino acid sequence set forth in SEQ ID NO: 2 and a heavy chain CDR3 having an amino acid sequence set forth in SEQ ID NO: 3, and a light chain variable region comprising a light chain CDR1 having an amino acid sequence set forth in SEQ ID NO: 5, a light chain CDR2 having an amino acid sequence set forth in SEQ ID NO: 6 and a light chain CDR3 having an amino acid sequence set forth in SEQ ID NO: 7;

(2) an antibody comprising a heavy chain variable region comprising a heavy chain CDR1 having an amino acid sequence set forth in SEQ ID NO: 9, a heavy chain CDR2 having an amino acid sequence set forth in SEQ ID NO: 10 and a heavy chain CDR3 having an amino acid sequence set forth in SEQ ID NO: 11, and a light chain variable region comprising a light chain CDR1 having an amino acid sequence set forth in SEQ ID NO: 13, a light chain CDR2 having an amino acid sequence set forth in SEQ ID NO: 14, and a light chain CDR3 having an amino acid sequence set forth in SEQ ID NO: 15;

(3) an antibody comprising a heavy chain variable region comprising a heavy chain CDR1 having an amino acid sequence set forth in SEQ ID NO: 17, a heavy chain CDR2 having an amino acid sequence set forth in SEQ ID NO: 18 and a heavy chain CDR3 having an amino acid sequence set forth in SEQ ID NO: 19, and a light chain variable region comprising a light chain CDR1 having an amino acid sequence set forth in SEQ ID NO: 21, a light chain CDR2 having an amino acid sequence set forth in SEQ ID NO: 22 and a light chain CDR3 having an amino acid sequence set forth in SEQ ID NO: 23; and (4) an antibody comprising
a heavy chain variable region comprising a heavy chain CDR1 having an amino acid sequence set forth in SEQ ID NO: 25, a heavy chain CDR2 having an amino acid sequence set forth in SEQ ID NO: 26 and a heavy chain CDR3 having an amino acid sequence set forth in SEQ ID NO: 27, and a light chain variable region comprising a light chain CDR1 having an amino acid sequence set forth in SEQ ID NO: 29, a light chain CDR2 having an amino acid sequence set forth in SEQ ID NO: 30, and a light chain CDR3 having an amino acid sequence set forth in SEQ ID NO: 31.

2. The antibody or an antigen-binding fragment thereof according to claim 1, wherein the antibody is (1) an antibody comprising a heavy chain variable region comprising a heavy chain CDR1 having an amino acid sequence set forth in SEQ ID NO: 1, a heavy chain CDR2 having an amino acid sequence set forth in SEQ ID NO: 2 and a heavy chain CDR3 having an amino acid sequence set forth in SEQ ID NO: 3, and a light chain variable region comprising a light chain CDR1 having an amino acid sequence set forth in SEQ ID NO: 5, a light chain CDR2 having an amino acid sequence set forth in SEQ ID NO: 6 and a light chain CDR3 having an amino acid sequence set forth in SEQ ID NO:7.

3. The antibody or an antigen-binding fragment thereof according to claim 2, comprising
a heavy chain variable region having an amino acid sequence of a heavy chain variable region set forth in SEQ ID NO: 4, and a light chain variable region having an amino acid sequence of a light chain variable region set forth in SEQ ID NO: 8.

4. The antibody or an antigen-binding fragment thereof according to claim 1, wherein the antibody is
(2) an antibody comprising a heavy chain variable region comprising a heavy chain CDR1 having an amino acid sequence set forth in SEQ ID NO: 9, a heavy chain CDR2 having an amino acid sequence set forth in SEQ ID NO: 10 and a heavy chain CDR3 having an amino acid sequence set forth in SEQ ID NO: 11, and a light chain variable region comprising a light chain CDR1 having an amino acid sequence set forth in SEQ ID NO: 13, a light chain CDR2 having an amino acid sequence set forth in SEQ ID NO: 14, and a light chain CDR3 having an amino acid sequence set forth in SEQ ID NO: 15.

5. The antibody or an antigen-binding fragment thereof according to claim 4, comprising a heavy chain variable region having an amino acid sequence of a heavy chain variable region set forth in SEQ ID NO: 12, and a light chain variable region having an amino acid sequence of a light chain variable region set forth in SEQ ID NO: 16.

6. The antibody or an antigen-binding fragment thereof according to claim 1, wherein the antibody is
(3) an antibody comprising a heavy chain variable region comprising a heavy chain CDR1 having an amino acid sequence set forth in SEQ ID NO: 17, a heavy chain CDR2 having an amino acid sequence set forth in SEQ ID NO: 18 and a heavy chain CDR3 having an amino acid sequence set forth in SEQ ID NO: 19, and a light chain variable region comprising a light chain CDR1 having an amino acid sequence set forth in SEQ ID NO: 21, a light chain CDR2 having an amino acid sequence set forth in SEQ ID NO: 22 and a light chain CDR3 having an amino acid sequence set forth in SEQ ID NO: 23.

7. The antibody or an antigen-binding fragment thereof according to claim 6, comprising a heavy chain variable region having an amino acid sequence of a heavy chain variable region set forth in SEQ ID NO: 20, and a light chain variable region having an amino acid sequence of a light chain variable region set forth in SEQ ID NO: 24.

8. The antibody or an antigen-binding fragment thereof according to claim 1, wherein the antibody is (4) an antibody comprising a heavy chain variable region comprising a heavy chain CDR1 having an amino acid sequence set forth in SEQ ID NO: 25, a heavy chain CDR2 having an amino acid sequence set forth in SEQ ID NO: 26 and a heavy chain CDR3 having an amino acid sequence set forth in SEQ ID NO: 27, and a light chain variable region comprising a light chain CDR1 having an amino acid sequence set forth in SEQ ID NO: 29, a light chain CDR2 having an amino acid sequence set forth in SEQ ID NO: 30, and a light chain CDR3 having an amino acid sequence set forth in SEQ ID NO: 31.

9. The antibody or an antigen-binding fragment thereof according to claim 8, comprising a heavy chain variable region having an amino acid sequence of a heavy chain variable region set forth in SEQ ID NO: 28, and a light chain variable region having an amino acid sequence of a light chain variable region set forth in SEQ ID NO: 32.

10. A method for detecting a cancer cell in a subject, comprising:

contacting the antibody according to claim 1 with a biological sample taken from the subject, and determining whether TMEM132A protein is present or not in the biological sample.

11. The method for detecting a cancer cell according to claim 10, wherein the antibody is selected from the group consisting of:

(1) an antibody comprising a heavy chain variable region comprising a heavy chain CDR1 having an amino acid sequence set forth in SEQ ID NO: 1, a heavy chain CDR2 having an amino acid sequence set forth in SEQ ID NO: 2 and a heavy chain CDR3 having an amino acid sequence set forth in SEQ ID NO: 3, and a light chain variable region comprising a light chain CDR1 having an amino acid sequence set forth in SEQ ID NO: 5, a light chain CDR2 having an amino acid sequence set forth in SEQ ID NO: 6 and a light chain CDR3 having an amino acid sequence set forth in SEQ ID NO: 7;

(2) an antibody comprising a heavy chain variable region comprising a heavy chain CDR1 having an amino acid sequence set forth in SEQ ID NO: 9, a heavy chain CDR2 having an amino acid sequence set forth in SEQ ID NO: 10 and a heavy chain CDR3 having an amino acid sequence set forth in SEQ ID NO: 11, and a light chain variable region comprising a light chain CDR1 having an amino acid sequence set forth in SEQ ID NO: 13, a light chain CDR2 having an amino acid sequence set forth in SEQ ID NO: 14, and a light chain CDR3 having an amino acid sequence set forth in SEQ ID NO: 15;

(3) an antibody comprising a heavy chain variable region comprising a heavy chain CDR1 having an amino acid sequence set forth in SEQ ID NO: 17, a heavy chain CDR2 having an amino acid sequence set forth in SEQ ID NO: 18 and a heavy chain CDR3 having an amino acid sequence set forth in SEQ ID NO: 19, and a light chain variable region comprising a light chain CDR1 having an amino acid sequence set forth in SEQ ID NO: 21, a light chain CDR2 having an amino acid sequence set forth in SEQ ID NO: 22, and a light chain CDR3 having an amino acid sequence set forth in SEQ ID NO: 23; and (4) an antibody comprising a heavy chain variable region comprising a heavy chain CDR1 having an amino acid sequence set forth in SEQ ID NO: 25, a heavy chain CDR2 having an amino acid sequence set forth in SEQ ID NO: 26 and a heavy chain CDR3 having an amino acid sequence set forth in SEQ ID NO: 27, and a light chain variable region comprising a light chain CDR1 having an amino acid sequence set forth in SEQ ID NO: 29, a light chain CDR2 having an amino acid sequence set forth in SEQ ID NO: 30, and a light chain CDR3 having an amino acid sequence set forth in SEQ ID NO: 31.

12. A method of treating cancer in a subject in need thereof, comprising administering an effective amount of an antibody according to claim 1.

* * * * *

SEQUENCE LISTING

```
<160> NUMBER OF SEQ ID NOS: 42

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1
```

```
Asn Tyr Ala Met Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Glu Val Ser Tyr Gly Gly Ser Tyr Thr Tyr Tyr Ser Asp Thr Val Thr
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Cys Gly Ser Asn Ser Ala Trp Phe Gly Phe
1               5                   10

<210> SEQ ID NO 4
<211> LENGTH: 137
<212> TYPE: PRT
<213> ORGANISM: Artificial Sequence
<220> FEATURE:
<223> OTHER INFORMATION: Synthetic Construct

<400> SEQUENCE: 4

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Arg
            20                  25                  30

Pro Gly Gly Ser Leu Lys Leu Ser Cys Ala Ala Ser Gly Phe Thr Phe
        35                  40                  45

Ser Asn Tyr Ala Met Ser Trp Val Arg Gln Ser Pro Glu Lys Arg Leu
    50                  55                  60

Glu Trp Val Ala Glu Val Ser Tyr Gly Gly Ser Tyr Thr Tyr Tyr Ser
65                  70                  75                  80

Asp Thr Val Thr Gly Arg Phe Thr Ile Ser Arg Asp Asn Ala Lys Asn
                85                  90                  95

Thr Leu Tyr Leu Asp Met Ser Ser Leu Arg Ser Glu Asp Ser Ala Ile
            100                 105                 110

Tyr Tyr Cys Val Arg Cys Gly Ser Asn Ser Ala Trp Phe Gly Phe Trp
        115                 120                 125

Gly Gln Gly Thr Leu Val Thr Val Ser
    130                 135

<210> SEQ ID NO 5
<211> LENGTH: 16
<212> TYPE: PRT
<213> ORGANISM: Artificial Sequence
<220> FEATURE:
<223> OTHER INFORMATION: Synthetic Construct

<400> SEQUENCE: 5

Lys Ser Ser Gln Ser Leu Leu Ser Asn Asn Gly Lys Thr Tyr Leu Asn
1               5                   10                  15
```

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Leu Val Ser Glu Leu Asp Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Val Gln Gly Thr His Phe Pro Tyr Thr
1               5

<210> SEQ ID NO 8
<211> LENGTH: 132
<212> TYPE: PRT
<213> ORGANISM: Artificial Sequence
<220> FEATURE:
<223> OTHER INFORMATION: Synthetic Construct

<400> SEQUENCE: 8

Met Met Ser Pro Ala Gln Phe Leu Phe Leu Leu Val Leu Trp Ile Gln
1               5                   10                  15

Glu Thr Lys Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Ser Asn Asn Gly Lys Thr Tyr Leu Asn Trp Leu Leu Gln Arg
    50                  55                  60

Pro Gly Gln Ser Pro Lys Arg Leu Ile Tyr Leu Val Ser Glu Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Tyr Thr Phe Gly Gly Gly Thr Lys
        115                 120                 125

Leu Glu Ile Lys
    130

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Ser Tyr Ala Met Ser
1               5

<210> SEQ ID NO 10

<211> LENGTH: 16
<212> TYPE: PRT
<213> ORGANISM: Artificial Sequence
<220> FEATURE:
<223> OTHER INFORMATION: Synthetic Construct

<400> SEQUENCE: 10

```
Glu Ile Ser Tyr Gly Gly Ser Phe Thr Tyr Tyr Pro Asp Thr Val Thr
1               5                   10                  15
```

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

```
Ala Gly Ser Asn Ser Ala Trp Leu Ser Tyr
1               5                   10
```

<210> SEQ ID NO 12
<211> LENGTH: 137
<212> TYPE: PRT
<213> ORGANISM: Artificial Sequence
<220> FEATURE:
<223> OTHER INFORMATION: Synthetic Construct

<400> SEQUENCE: 12

```
Met Asn Leu Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Ser Pro Glu Lys Arg Leu
    50                  55                  60

Glu Trp Val Ala Glu Ile Ser Tyr Gly Gly Ser Phe Thr Tyr Tyr Pro
65                  70                  75                  80

Asp Thr Val Thr Gly Arg Phe Thr Ile Ser Arg Asp Asn Val Lys Asn
                85                  90                  95

Ile Leu Tyr Leu Glu Met Ser Ser Leu Met Ser Glu Asp Thr Ala Met
            100                 105                 110

Tyr Tyr Cys Val Arg Ala Gly Ser Asn Ser Ala Trp Leu Ser Tyr Trp
        115                 120                 125

Gly Gln Gly Thr Leu Val Thr Val Ser
    130                 135
```

<210> SEQ ID NO 13
<211> LENGTH: 16
<212> TYPE: PRT
<213> ORGANISM: Artificial Sequence
<220> FEATURE:
<223> OTHER INFORMATION: Synthetic Construct

<400> SEQUENCE: 13

```
Lys Ser Ser Gln Ser Leu Leu Ser Ser Asn Gly Lys Ala Tyr Leu Asn
1               5                   10                  15
```

<210> SEQ ID NO 14
<211> LENGTH: 7
<212> TYPE: PRT
<213> ORGANISM: Artificial Sequence

```
<220> FEATURE:
<223> OTHER INFORMATION: Synthetic Construct

<400> SEQUENCE: 14

Leu Val Ser Glu Leu Asp Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Val Gln Gly Thr His Phe Pro Tyr Thr
1               5

<210> SEQ ID NO 16
<211> LENGTH: 132
<212> TYPE: PRT
<213> ORGANISM: Artificial Sequence
<220> FEATURE:
<223> OTHER INFORMATION: Synthetic Construct

<400> SEQUENCE: 16

Met Met Ser Pro Ala Gln Phe Leu Phe Leu Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Gln Ser
        35                  40                  45

Leu Leu Ser Ser Asn Gly Lys Ala Tyr Leu Asn Trp Leu Leu Gln Arg
    50                  55                  60

Pro Gly Gln Ser Pro Lys Arg Leu Ile Tyr Leu Val Ser Glu Leu Asp
65                  70                  75                  80

Ser Gly Val Pro Asp Arg Phe Thr Gly Ser Gly Ser Gly Thr Gly Phe
                85                  90                  95

Thr Leu Lys Ile Ser Arg Val Glu Ala Glu Asp Leu Gly Ile Tyr Tyr
            100                 105                 110

Cys Val Gln Gly Thr His Phe Pro Tyr Thr Phe Gly Gly Gly Thr Lys
        115                 120                 125

Leu Glu Ile Lys
    130

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Ser Ser Ala Met Ser
1               5

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 18

Glu Ile Ser Tyr Gly Gly Ser Tyr Thr Tyr Tyr Pro Asp Thr Val Thr
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Gly Gly Ser Asn Ser Ala Trp Phe Ala Tyr
1               5                   10

<210> SEQ ID NO 20
<211> LENGTH: 137
<212> TYPE: PRT
<213> ORGANISM: Artificial Sequence
<220> FEATURE:
<223> OTHER INFORMATION: Synthetic Construct

<400> SEQUENCE: 20

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Ser Ala Met Ser Trp Val Arg Gln Ser Pro Glu Lys Arg Leu
    50                  55                  60

Glu Trp Val Gly Glu Ile Ser Tyr Gly Gly Ser Tyr Thr Tyr Tyr Pro
65                  70                  75                  80

Asp Thr Val Thr Gly Arg Phe Thr Ile Ser Arg Asp Asn Ala Lys Asn
                85                  90                  95

Thr Leu Tyr Leu Glu Met Ser Ser Leu Arg Ser Glu Asp Thr Ala Met
            100                 105                 110

Tyr Tyr Cys Val Arg Gly Gly Ser Asn Ser Ala Trp Phe Ala Tyr Trp
        115                 120                 125

Gly Gln Gly Thr Leu Val Thr Val Ser
    130                 135

<210> SEQ ID NO 21
<211> LENGTH: 16
<212> TYPE: PRT
<213> ORGANISM: Artificial Sequence
<220> FEATURE:
<223> OTHER INFORMATION: Synthetic Construct

<400> SEQUENCE: 21

Lys Ser Ser Gln Arg Leu Leu Tyr Ser Asn Gly Lys Thr Tyr Leu Asn
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Leu Val Ser Lys Leu Asp Ser
```

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Val Gln Gly Thr His Phe Pro Tyr Thr
1               5

<210> SEQ ID NO 24
<211> LENGTH: 132
<212> TYPE: PRT
<213> ORGANISM: Artificial Sequence
<220> FEATURE:
<223> OTHER INFORMATION: Synthetic Construct

<400> SEQUENCE: 24

Met Met Ser Pro Ala Gln Phe Leu Ser Leu Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Thr Cys Lys Ser Ser Gln Arg
        35                  40                  45

Leu Leu Tyr Ser Asn Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asn Arg Phe Thr Asp Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Tyr Thr Phe Gly Gly Gly Thr Lys
        115                 120                 125

Leu Glu Ile Lys
    130

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct

<400> SEQUENCE: 25

Ser Asp Tyr Tyr Trp Asn
1               5

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Tyr Ile Arg Tyr Asp Gly Tyr Asn Ala Tyr Asn Pro Ser Leu Lys
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Asn Asp Tyr Asp Gly Tyr Tyr Phe Asp Asn
1               5                   10

<210> SEQ ID NO 28
<211> LENGTH: 136
<212> TYPE: PRT
<213> ORGANISM: Artificial Sequence
<220> FEATURE:
<223> OTHER INFORMATION: Synthetic Construct

<400> SEQUENCE: 28

Met Lys Val Leu Ser Leu Leu Tyr Leu Leu Thr Ala Ile Pro Gly Ala
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Tyr Ser Ile Thr
            35                  40                  45

Ser Asp Tyr Tyr Trp Asn Trp Ile Arg Gln Phe Pro Gly Asn Lys Leu
        50                  55                  60

Glu Trp Met Gly Tyr Ile Arg Tyr Asp Gly Tyr Asn Ala Tyr Asn Pro
65                  70                  75                  80

Ser Leu Lys Ser Arg Ile Ser Ile Thr Arg Asp Thr Ser Lys Asn Gln
                85                  90                  95

Phe Leu Leu Lys Leu Lys Ser Val Thr Thr Glu Asp Thr Ala Thr Tyr
                100                 105                 110

Phe Cys Ala Arg Asn Asp Tyr Asp Gly Tyr Tyr Phe Asp Asn Trp Gly
            115                 120                 125

Gln Gly Thr Thr Leu Thr Val Ser
        130                 135

<210> SEQ ID NO 29
<211> LENGTH: 17
<212> TYPE: PRT
<213> ORGANISM: Artificial Sequence
<220> FEATURE:
<223> OTHER INFORMATION: Synthetic Construct

<400> SEQUENCE: 29

Lys Ser Ser Gln Ser Leu Leu Tyr Ser Thr Asn Gln Lys Asn Tyr Leu
1               5                   10                  15

Ala

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Trp Ala Ser Thr Arg Glu Ser
1               5

<210> SEQ ID NO 31

<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Gln Gln Tyr Tyr Thr Asn Pro Tyr Thr
1               5

<210> SEQ ID NO 32
<211> LENGTH: 133
<212> TYPE: PRT
<213> ORGANISM: Artificial Sequence
<220> FEATURE:
<223> OTHER INFORMATION: Synthetic Construct

<400> SEQUENCE: 32

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Thr Asn Gln Lys Asn Tyr Leu Ala Trp Tyr Gln Gln
        50                  55                  60

Lys Pro Gly Gln Ser Pro Gln Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Ser Ala Glu Asp Leu Ala Val Tyr
                100                 105                 110

Tyr Cys Gln Gln Tyr Tyr Thr Asn Pro Tyr Thr Phe Gly Gly Gly Ala
            115                 120                 125

Lys Leu Glu Ile Lys
    130

<210> SEQ ID NO 33
<211> LENGTH: 29
<212> TYPE: DNA
<213> ORGANISM: Artificial Sequence
<220> FEATURE:
<223> OTHER INFORMATION: Synthetic Construct

<400> SEQUENCE: 33
catatgttcc acctcaaagg gcaggattg                                    29

<210> SEQ ID NO 34
<211> LENGTH: 31
<212> TYPE: DNA
<213> ORGANISM: Artificial Sequence
<220> FEATURE:
<223> OTHER INFORMATION: Synthetic Construct

<400> SEQUENCE: 34
gtcgaccttg aagcggtcta gcttggcagt c                                 31

<210> SEQ ID NO 35
<211> LENGTH: 30
<212> TYPE: DNA
<213> ORGANISM: Artificial Sequence
<220> FEATURE:
<223> OTHER INFORMATION: Synthetic Construct

<400> SEQUENCE: 35
catatgaata cagcaccact gactggagtg                                              30

<210> SEQ ID NO 36
<211> LENGTH: 33
<212> TYPE: DNA
<213> ORGANISM: Artificial Sequence
<220> FEATURE:
<223> OTHER INFORMATION: Synthetic Construct

<400> SEQUENCE: 36
gtcgacttcc agagaggcta cacgcgagtc cag                                          33

<210> SEQ ID NO 37
<211> LENGTH: 45
<212> TYPE: DNA
<213> ORGANISM: Artificial Sequence
<220> FEATURE:
<223> OTHER INFORMATION: Synthetic Construct

<400> SEQUENCE: 37
ctaatacgac tcactatagg gcaagcagtg gtatcaacgc agagt                             45

<210> SEQ ID NO 38
<211> LENGTH: 22
<212> TYPE: DNA
<213> ORGANISM: Artificial Sequence
<220> FEATURE:
<223> OTHER INFORMATION: Synthetic Construct

<400> SEQUENCE: 38
ctaatacgac tcactatagg gc                                                      22

<210> SEQ ID NO 39
<211> LENGTH: 29
<212> TYPE: DNA
<213> ORGANISM: Artificial Sequence
<220> FEATURE:
<223> OTHER INFORMATION: Synthetic Construct

<400> SEQUENCE: 39
cccatggcca ccarattcty atcagacag                                               29

<210> SEQ ID NO 40
<211> LENGTH: 45
<212> TYPE: DNA
<213> ORGANISM: Artificial Sequence
<220> FEATURE:
<223> OTHER INFORMATION: Synthetic Construct

<400> SEQUENCE: 40
ctaatacgac tcactatagg gcaagcagtg gtatcaacgc agagt                             45

<210> SEQ ID NO 41
<211> LENGTH: 22
<212> TYPE: DNA
<213> ORGANISM: Artificial Sequence
<220> FEATURE:
<223> OTHER INFORMATION: Synthetic Construct

<400> SEQUENCE: 41
ctaatacgac tcactatagg gc                                                      22

<210> SEQ ID NO 42

```
<211> LENGTH: 28
<212> TYPE: DNA
<213> ORGANISM: Artificial Sequence
<220> FEATURE:
<223> OTHER INFORMATION: Synthetic Construct

<400> SEQUENCE: 42
gttgttcawg argcacacga ctgaggca                                      28
```